(12) United States Patent
Kemp

(10) Patent No.: US 11,004,560 B2
(45) Date of Patent: May 11, 2021

(54) GENERATING A MAP OF A MEDICAL FACILITY

(71) Applicant: Axon Acuity, LLC, Roanoke, VA (US)

(72) Inventor: Tammy S. Kemp, Roanoke, VA (US)

(73) Assignee: AXON ACUITY, LLC, Roanoke, VA (US)

( * ) Notice: Subject to any disclaimer, the term of this patent is extended or adjusted under 35 U.S.C. 154(b) by 334 days.

(21) Appl. No.: 15/912,614

(22) Filed: Mar. 6, 2018

(65) Prior Publication Data

US 2018/0197632 A1    Jul. 12, 2018

Related U.S. Application Data

(63) Continuation of application No. 14/209,439, filed on Mar. 13, 2014, now Pat. No. 9,946,840.

(60) Provisional application No. 61/896,980, filed on Oct. 29, 2013, provisional application No. 61/785,407, filed on Mar. 14, 2013.

(51) Int. Cl.
*G16H 40/20* (2018.01)
*G16H 10/60* (2018.01)
*G16H 50/30* (2018.01)
*G16H 20/10* (2018.01)
*G16H 20/40* (2018.01)

(52) U.S. Cl.
CPC .............. *G16H 40/20* (2018.01); *G16H 10/60* (2018.01); *G16H 50/30* (2018.01); *G16H 20/10* (2018.01); *G16H 20/40* (2018.01)

(58) Field of Classification Search
CPC ........ G16H 40/20; G16H 10/60; G16H 50/30; G16H 20/10; G16H 20/40
See application file for complete search history.

(56) References Cited

U.S. PATENT DOCUMENTS

| 7,752,096 | B2 | 7/2010 | Santalo et al. | |
|---|---|---|---|---|
| 2006/0004605 | A1* | 1/2006 | Donoghue | G16H 10/60 705/2 |
| 2006/0287906 | A1* | 12/2006 | McGillin | G06Q 10/06 705/2 |
| 2011/0205062 | A1 | 8/2011 | Pesot et al. | |
| 2014/0222455 | A1 | 8/2014 | Horn et al. | |

\* cited by examiner

*Primary Examiner* — Linh Giang Le
(74) *Attorney, Agent, or Firm* — Coats & Bennett, PLLC

(57) ABSTRACT

A computing device retrieves patient data for a plurality of patients assigned to healthcare unit of a medical facility, and scores a mortality risk of the patients from the patient data. The computing device then generates a map of the medical facility comprising an illustration of a layout of the medical facility, and a visual representation of an area within the illustration of the layout that indicates where the healthcare unit is located within the medical facility. The map further comprises a labeling of the healthcare unit with a visual indication of the mortality risk of the patients in the healthcare unit. The computing device then sends the map to a display device.

13 Claims, 47 Drawing Sheets

Table 1

| Patient Indicator | Weighted Score |
|---|---|
| Patient admitted | 3 if admitted 2 hours ago<br>2 if admitted 2-4 hours ago<br>1 if admitted 4-6 hours ago<br>0 if admitted more than 6 hours ago |
| Respiratory rate | 3 if significant respiratory issues ie cheynestoke<br>2 if moderate respiratory issues, ie moderate retractions, stridor<br>1 if minor respiratory issues ie mild atelectosis<br>0 if normal for age and weight<br><br>adjust for age and weight |
| Skin (Braden score) | 4 if less than or equal to 9<br>3 if between 10-12<br>2 if between 13-14<br>1 if between 15-18<br>0 if greater than 18<br><br>OR<br>Adjust for Age and Weight<br>Example Braden Q Score<br>4 if less than or equal to 7<br>3 if between 8-10<br>2 if between 11-12<br>1 if between 13-16<br>0 if greater than 16 |
| Morse Score | 1 if greater than or equal to 45<br>0 of less than 45<br><br>Adjust for age and weight |
| Neuro (RASS) | 1 if greater than or equal to 2 and less than or equal to -2<br>0 for all other conditions<br>Adjust for age and weight |
| Drains/Airway | 1 if any lines<br>0 if no lines<br>Adjust for age and weight |
| Chemotherapy or Radiation | 2 if day 1<br>1 if > or equal day 1<br>0 not present<br>Adjust for age and weight |
| Wounds | 1 if any wounds<br>0 if no wounds<br>Adjust for age and weight |
| Medication administered | 1 if any medication administered/action taken<br>0 if no medication administered/action has taken place<br>Adjust for age and weight, |
| Volume of medication | 4<br>3<br>2<br>1<br>0 if no medication administered |

FIG. 1

Table 1 (cont.)

| Patient Indicator | Weighted Score |
|---|---|
| Patient admitted | 3 if admitted 2 hours ago<br>2 if admitted 2-4 hours ago<br>1 if admitted 4-6 hours ago<br>0 if admitted more than 6 hours ago |
| Sitter one on one assignment (safety, suicide) | 1 if required<br>0 if not required<br>Adjust for age and weight |
| Respiratory rate | 3 if significant respiratory issues<br>2 if moderate respiratory issues<br>1 if minor respiratory issues<br>0 if no respiratory issues |
| Skin (Braden score) | 4 if less than or equal to 9<br>3 if between 10-12<br>2 if between 13-14<br>1 if between 15-18<br>0 if greater than 18 |
| Morse Score | 1 if greater than or equal to 45<br>0 of less than 45<br>Adjust for age and weight |
| Neuro (RASS) | 1 if greater than or equal to 2 and less than or equal to -2<br>0 for all other conditions<br>Adjust based on age and weight |
| Drains/ Airway may include (Burns, hemodialysis, pressure ulcers, hemodynamic and central monitoring, wounds, airways) | 2 if greater than =7<br>1 if any<br>0 if no lines<br>Adjust for age and weight |
| Wounds | 1 if any wounds<br>0 if no wounds |
| Medication administered | 1 if any medication administered<br>0 if no medication administered |
| Volume of medication | 4 If >=95<br>3 if 80-94<br>2 If 65-79<br>1 if 49- 64<br>0 if no medication administered or less than 49<br>Adjust for age and weight |
| Volume of drips<br>example introbes, antihypertensives, vasopressors, platets, sedatives, antiarrythmics, inotropes, other IV speciality drips | 4 If >= 4 drips<br>3 if > = 3 drips<br>2 If >= 2 drips<br>1 If >=1 drip<br>0 no drips<br>Adjust by age and weight and level of medication |
| CIWA score | 1 if present<br>0 not present<br>Adjust by age and weight |
| Isolation precautions | 2 if on isolation precautions<br>0 if no isolation precautions |
| Weight | 2 if weight greater than 300 pounds or less than 1500 grams<br>1 if weight above normal weight or below normal weight<br>0 if weight normal |
| Blood Products | 1 if any blood products received<br>0 if no blood products received |

FIG. 2

Table 1 (cont.)

| Patient Indicators (cont.) | Weighted score |
|---|---|
| Bipap supportive airway | If present score of 1<br>Adjust for age and weight |
| Vascular cap refill/ color | 4 if 4 standard deviations above/below normal<br>3 if 3 standard deviations above/below normal<br>2 if 2 standard deviations above/below normal<br>1 if 1 standard deviation above/below normal<br>0 if normal for age<br><br>Or<br><br>Score of 3 if cap refill >5 secs / blue in all 4 extremities<br>Score of 2 if cap refill 5 secs/mottled in all 4 extremities<br>Score of 1 if cap refill 4 secs/ pale in all 4 extremities<br>Score of 0 if cap refil <3 secs/pink in all 4 extremities<br><br>Adjust for age, weight and number of extremities impacted |
| Cognitive/ perceptual/Neurological | 4 if 4 standard deviations above/below normal<br>3 if 3 standard deviations above/below normal<br>2 if 2 standard deviations above/below normal<br>1 if 1 standard deviation above/below normal<br>0 if normal for age<br><br>Or :<br>Score of 3 for Glascow Coma Score of 15<br>Score of 2 for Glascow Coma Score of 13-14<br>Score of 1 for Glascow Coma Score of 10-12<br>Score of 0 for Glascow Coma Score of 3-9<br><br>Or:<br>0 pupils fixed and dilated, no response to pain<br>1 Pupils non equal, response to pain only, coma<br>2 awake , alert not oriented<br>3 awake alert oriented to person, place and time<br><br>Adjust to account for age and weight |
| Urine output | 4 if 4 standard deviations above/below normal<br>3 if 3 standard deviations above/below normal<br>2 if 2 standard deviations above/below normal<br>1 if 1 standard deviation above/below normal<br>0 if normal for age<br><br>OR<br>2 if urine output >3 cc/kg/hr<br>3 if urine output is 1.1 cc/kg/hr<br>2 if urine output is .5 cc/kg/hr<br>1 if urine output is >.01 cc/kg/hr<br>0 If urine output is 0 cc/kg/hr<br><br>Adjust to account for age and weight |

FIG. 3

Table 1 (cont.)

| Patient Indicator (cont.) | Weighted Score |
|---|---|
| Hemodialysis (continuous renal replacement therapy) | 2 if hemodialysis<br>0 if no hemodialysis |
| Ventriculostomy | 3 if ventriculostomy present<br>0 if no ventriculostomy |
| Ventricular Assist Device (VAD) | 2 if VAD<br>0 if no VAD |
| Intra-aortic Balloon Counterpulsation pump (IAPB) / ECMO | 2 if IAPB<br>0 if no IAPB |
| Hypothermia | 3 if hypothermia at hour 0<br>2 if hypothermia between hour 0 and hour 1<br>1 if hypothermia between hour 1 and hour 2<br>0 if hypothermia after hour 2 |
| Interpreter | 1 if interpreter required<br>0 if no interpreter required |
| Mean Corpuscular Volume (MCV) | 4 if 4 standard deviations above/below normal<br>3 if 3 standard deviations above/below normal<br>2 if 2 standard deviations above/below normal<br>1 if 1 standard deviation above/below normal<br>0 if normal |
| Red Blood Count | 4 if 4 standard deviations above/below normal<br>3 if 3 standard deviations above/below normal<br>2 if 2 standard deviations above/below normal<br>1 if 1 standard deviation above/below normal<br>0 if normal |
| Platelets | 4 if 4 standard deviations above/below normal<br>3 if 3 standard deviations above/below normal<br>2 if 2 standard deviations above/below normal<br>1 if 1 standard deviation above/below normal<br>0 if normal |
| Iron | 4 if 4 standard deviations above/below normal<br>3 if 3 standard deviations above/below normal<br>2 if 2 standard deviations above/below normal<br>1 if 1 standard deviation above/below normal<br>0 if normal |
| Transferrin | 4 if 4 standard deviations above/below normal<br>3 if 3 standard deviations above/below normal<br>2 if 2 standard deviations above/below normal<br>1 if 1 standard deviation above/below normal<br>0 if normal |
| CD4% | 4 if 4 standard deviations above/below normal<br>3 if 3 standard deviations above/below normal<br>2 if 2 standard deviations above/below normal<br>1 if 1 standard deviation above/below normal<br>0 if normal |

FIG. 4A

Table 1 (cont.)

| Patient Indicator (cont.) | Weighted Score |
|---|---|
| Carbon dioxide | 4 if 4 standard deviations above/below normal<br>3 if 3 standard deviations above/below normal<br>2 if 2 standard deviations above/below normal<br>1 if 1 standard deviation above/below normal<br>0 if normal |
| Lactic acid | 4 if 4 standard deviations above/below normal<br>3 if 3 standard deviations above/below normal<br>2 if 2 standard deviations above/below normal<br>1 if 1 standard deviation above/below normal<br>0 if normal |
| $pO_2$ | 4 if 4 standard deviations above/below normal<br>3 if 3 standard deviations above/below normal<br>2 if 2 standard deviations above/below normal<br>1 if 1 standard deviation above/below normal<br>0 if normal |
| White Blood Cell Count | 4 if 4 standard deviations above/below normal<br>3 if 3 standard deviations above/below normal<br>2 if 2 standard deviations above/below normal<br>1 if 1 standard deviation above/below normal<br>0 if normal |
| Hematocrit | 4 if 4 standard deviations above/below normal<br>3 if 3 standard deviations above/below normal<br>2 if 2 standard deviations above/below normal<br>1 if 1 standard deviation above/below normal<br>0 if normal |
| International Normalized Ratio | 4 if 4 standard deviations above/below normal<br>3 if 3 standard deviations above/below normal<br>2 if 2 standard deviations above/below normal<br>1 if 1 standard deviation above/below normal<br>0 if normal |
| Creatine | 4 if 4 standard deviations above/below normal<br>3 if 3 standard deviations above/below normal<br>2 if 2 standard deviations above/below normal<br>1 if 1 standard deviation above/below normal<br>0 if normal |

FIG. 4B

| | |
|---|---|
| Respiratory Rate per minute | 4 if 4 standard deviations above/below normal<br>3 if 3 standard deviations above/below normal<br>2 if 2 standard deviations above/below normal<br>1 if 1 standard deviation above/below normal<br>0 if normal for age<br><br>Or<br>1 if respiratory rate <= 8 per minute<br>2 if respiratory rate 9 -14 per minute or 21-29 per minute<br>3 if respiratory rate 15-20 per minute<br>1 If respiratory rate 21-29 per minute<br>0 if respiratory rate >=30 per minute<br><br>Adjust to account for age and weight |
| Body temperature | 4 if 4 standard deviations above/below normal<br>3 if 3 standard deviations above/below normal<br>2 if 2 standard deviations above/below normal<br>1 if 1 standard deviation above/below normal<br>0 if normal for age<br><br>Or<br>1 if temperature is <=35 degree Celsius <=95<br>2 if temperature is 95.1-96.8 F<br>3 if temperature is 35.1- 38.4 degree Celsius or 98.9-100.4<br>2 if temperature is 100.5-101.4 F<br>1 if temperature is 38.5 degree Celsius or 101.5 F<br>Adjust to account for age |
| Code Blue | 5 at time 0 hour to 1 hour<br>4 at time 1 hour to 2 hours<br>3 at time 2 hours to 3 hours<br>2 at time 3 hours to 4 hours<br>1 at time 4 hours to 5 hours<br>0 at time greater than 5 hours |
| Rapid Response | 3 at time 0 hour to 1 hour<br>2 at time 1 hour to 2 hours<br>1 at time 2 hours to 3 hours<br>0 at time greater than 3 hours |
| Discharge | 2 if discharged at time 0 hour to 1 hours<br>1 if discharged at time 1 hour to time 2 hours<br>0 if discharged for more than 2 hours |
| Death | 1 If dead/palliative<br>0 if alive |
| Post catherization | 2 at time 0 hour to 1 hour<br>1 at time 1 hour to 2 hours<br>0 after 2 hours post catherization |
| pH | 4 if 4 standard deviations above/below normal<br>3 if 3 standard deviations above/below normal<br>2 if 2 standard deviations above/below normal<br>1 if 1 standard deviation above/below normal<br>0 if normal |

FIG. 4C

Table 1 (cont.)

| Patient Indicator (cont.) | Weighted Score |
|---|---|
| Volume of drips | 4<br>3<br>2<br>1<br>0 |
| Isolation precautions | 1 if on isolation precautions<br>0 if no isolation precautions |
| Weight | 2 if weight greater than 300 pounds<br>1 if weight above normal weight or below normal weight<br>0 if weight normal |
| Blood Products | 1 if any blood products received<br>0 if no blood products received |
| Blood Pressure systolic/diasystolic | 4 if 4 standard deviations above/below normal<br>3 if 3 standard deviations above/below normal<br>2 if 2 standard deviations above/below normal<br>1 if 1 standard deviation above/below normal<br>0 if normal for age<br><br>Or<br>systolic blood pressure:<br>0 if blood pressure <70<br>1 if blood pressure 71-80<br>2 if blood pressure 81-100<br>3 if blood pressure 101-199<br>1 if blood pressure>= 200<br>or like pattern for diasystolic<br><br>Adjust to account for age and weight |
| Heart Rate per minute | 4 if 4 standard deviations above/below normal<br>3 if 3 standard deviations above/below normal<br>2 if 2 standard deviations above/below normal<br>1 if 1 standard deviation above/below normal<br>0 if normal for age<br><br>Or<br>1 if heart rate <40 beats per minute<br>2 if heart rate 40-50 beats per minute<br>3 if heart rate 51-100 beats per minute<br>2 if heart rate 101=110 beats per minute<br>1 if heart rate 111-129 beats per minute<br>0 if heart rate >=130 beats per minute<br><br>Adjust to account for age and weight |

FIG. 4D

| Lab Result | Condition (all "OR") | Score |
|---|---|---|
| Lactic Acid | = (none) | 0 |
| | < 2 | 0.1 |
| | < 4 | 1 |
| | < 6 | 2 |
| | >= 6 | 3 |
| | | |
| phABG | = (none) | 0 |
| | < 7.25 | 3 |
| | < 7.3 | 2 |
| | < 7.35 | 1 |
| | <= 7.45 | 0.1 |
| | > 7.45 | 1 |
| | | |
| PO2 | = (none) | 0 |
| | < 50 | 3 |
| | < 60 | 2 |
| | < 75 | 1 |
| | >= 75 | 0.1 |
| | | |
| Base Excess | = (none) | 0 |
| | <= -6 | 3 |
| | <= -5 | 2 |
| | <= -4 | 1 |
| | < -2 | 0.2 |
| | <= 2 | 0.1 |

FIG. 5B

| Lab Result | Condition (all "OR") | Score |
|---|---|---|
| | < 4 | 0.2 |
| | < 5 | 1 |
| | < 6 | 2 |
| | >= 6 | 3 |
| | | |
| Base Deficit | = (none) | 0 |
| | <= -6 | 3 |
| | <= -5 | 2 |
| | <= -4 | 1 |
| | < -2 | 0.2 |
| | <= 2 | 0.1 |
| | < 4 | 0.2 |
| | < 5 | 1 |
| | < 6 | 2 |
| | >= 6 | 3 |
| | | |
| Base Excess or Base Deficit | Base Excess Score > 0 | Base Excess Score |
| | Base Deficit Score > 0 | Base Deficit Score |
| | | |
| SpO2 | = (none) | 0 |
| | <= 60 | 3 |
| | < 74 | 2 |
| | < 92 | 1 |
| | >= 92 | 0.1 |
| | | |
| PO2 or SpO2 | PO2 Score > 0 | PO2 Score |
| | SpO2 Score > 0 | SpO2 Score |

FIG. 5C

| | | |
|---|---|---|
| IonizedCalcium | score 0 = 4.5-5.4mg/dl; score 1= 5.5-5.9 mg/dl ; score 2= 2-3 or 6-6.9mg/dl; score 3 = <2 or >7mg/dl | 0= normal for age, height, sex and weight range as appropriate, 1, 2, 3, 4 Standard Deviation or |
| NA | score 0 = 135-144 meq/L ; score 1= 126-134meq/L or 145- 155 meq/L ; score 2= 120-125meq/L or 156-179meq/L score 3= <120meq/L or >180meq/L | 0= normal for age, height, sex and weight range as appropriate, 1, 2, 3, 4 Standard Deviation or |
| K | score 0= 3.6-5.5 meq/L; score1= 3.0-3.5 meq/L or 5.5- 5.9meq/L; score of 2=2.6-3.4meq/L or 6-7meq/L; score of 3 = <2.5meq/L or >7 meq/L | 0= normal for age, height, sex and weight range as appropriate, 1, 2, 3, 4 Standard Deviation or |
| Glucose | score0 =70-125mg/dl; score 1=60-70mg/dl or126-150mg/dl; score 2= 50-59mg/dl or 151mg/dl-249 score 3= <50mg/dl or >250mg/dl; | 0= normal for age, height, sex and weight range as appropriate, 1, 2, 3, 4 Standard Deviation or |
| PT/PTT | score 0= 10-12 seconds for PT and 30-45 seconds | 0= normal for age, height, sex and weight range as appropriate, 1, 2, 3, 4 Standard Deviation or |

FIG. 5D

| | | |
|---|---|---|
| Creatinine | score 0-.5-1.3mg/dl | 0= normal for age, height, sex and weight range as appropriate, 1, 2, 3, 4 Standard Deviation or |
| HCT | Score 0 birth= 44-64%; 14-90 days= 35-49%; 6month-1year= 30-40%; 4-10year= 31-43 | 0= normal for age, height, sex and weight range as appropriate, 1, 2, 3, 4 Standard Deviation or |
| Cerebral perfusion pressure | Score 0 = 40-50 mmHg | 0= normal for age, height, sex and weight range as appropriate, 1, 2, 3, 4 Standard Deviation or |
| Pulmonary Artery Pressure | score 0 = 15-30mmHg systolic; 5-10mmHG diasystolic | 0= normal for age, height, sex and weight range as appropriate, 1, 2, 3, 4 Standard Deviation or |
| Central Venous Pressure | Score 0= 1-5 mm Hg | 0= normal for age, height, sex and weight range as appropriate, 1, 2, 3, 4 Standard Deviation or |
| Cardiac Output | Score 0-= 4- 5 L | 0= normal for age, height, sex and weight range as appropriate, 1, 2, 3, 4 Standard Deviation or |
| Albumin | score 0 = 3.4-5.0 g/100ml ; score 1= 2.9-3.3g/100ml or > 5.1 g/100 ml score 2= 2.4-2.8g/100ml score 3= < 2.4 | 0= normal for age, height, sex and weight range as appropriate, 1, 2, 3, 4 Standard Deviation or |
| HBA1C | score 0= <5; score 1= 5.8-6.4; score 2= 6.5-7.0; score 3 = >7.1 percent | 0= normal for age, height, sex and weight range as appropriate, 1, 2, 3, 4 Standard Deviation or |
| BUN | score 0= 4-8mg/dl | 0= normal for age, height, sex and weight range as appropriate, 1, 2, 3, 4 Standard Deviation or |
| Bilirubin | score 0=.25-.8mg/dl | 0= normal for age, height, sex and weight range as appropriate, 1, 2, 3, 4 Standard Deviation or |
| NH3 | score 0= 18-48mcg/dl adult; 45-80mcg/dl child; 95-150 newborn | 0= normal for age, height, sex and weight range as appropriate, 1, 2, 3, 4 Standard Deviation or |

FIG. 5E

| | | |
|---|---|---|
| CPK | score 0= <=70 | 0= normal for age, height, sex and weight range as appropriate, 1, 2, 3, 4 Standard Deviation or |
| Intercranial Pressure | score 0= <15mmHg | 0= normal for age, height, sex and weight range as appropriate, 1, 2, 3, 4 Standard Deviation or |
| specific gravity | score 0 = 1.002-1.045 | 0= normal for age, height, sex and weight range as appropriate, 1, 2, 3, 4 Standard Deviation or |
| SGOT | score 0= 5-20IU/L | 0= normal for age, height, sex and weight range as appropriate, 1, 2, 3, 4 Standard Deviation or |
| SGPT | score 0= 4-25IU/L | 0= normal for age, height, sex and weight range as appropriate, 1, 2, 3, 4 Standard Deviation or |
| Cardiac Index | score 0 = 2.6 L/min - 4.2L/min | 0= normal for age, height, sex and weight range as appropriate, 1, 2, 3, 4 Standard Deviation or |
| Right Arterial Pressure | Score 0= 1-5 mm Hg | 0= normal for age, height, sex and weight range as appropriate, 1, 2, 3, 4 Standard Deviation or |
| Left Arterial Pressure | score 0 = 5-10mmHg | 0= normal for age, height, sex and weight range as appropriate, 1, 2, 3, 4 Standard Deviation or |
| Pulmonary Capillary Wedge Pressure | score 0= 5-10mmHg | 0= normal for age, height, sex and weight range as appropriate, 1, 2, 3, 4 Standard Deviation or |
| urine output | score 0= >.5ml/kg/hour infant; >1 ml/kg/hour child | 0= normal for age, height, sex and weight range as appropriate, 1, 2, 3, 4 Standard Deviation or |
| Hemaglobin | score 0= 14-24g/dl birth; 11-17g/dl 1month old; 11-15g/dl 1 year old; 9-13g/dl 9-13 year old | 0= normal for age, height, sex and weight range as appropriate, 1, 2, 3, 4 Standard Deviation or |
| Mg | score 0= 1.2-1.8meq/L; | 0= normal for age, height, sex and weight range as appropriate, 1, 2, 3, 4 Standard Deviation or |
| PO4 | score 0= 4.5-6.8mg/dl (4-8 months old); 4.6-5.7mg/dl (1-2 year old); 4.2- 5.7 mg/dl (6 year old); 4.0-5.5mg/dl (>=10 year old) | 0= normal for age, height, sex and weight range as appropriate, 1, 2, 3, 4 Standard Deviation or |
| Ejection Fracture | | 0= normal for age, height, sex and weight range as appropriate, 1, 2, 3, 4 Standard Deviation or |
| INR | score 0= 1 to 2 | 0= normal for age, height, sex and weight range as appropriate, 1, 2, 3, 4 Standard Deviation or |
| Calcium Total | score 0 = 8.8-10.2 | 0= normal for age, height, sex and weight range as appropriate, 1, 2, 3, 4 Standard Deviation or |

FIG. 5F

Table 2

| Patient Composite Score | Compressed Score |
|---|---|
| 0-5 | 1 |
| 6-10 | 2 |
| 11-15 | 3 |
| 16-20 | 4 |
| 21-25 | 5 |
| 26-30 | 6 |
| 31-35 | 7 |
| 36-40 | 8 |
| 41-45 | 9 |
| 46+ | 10 |

Table 3

| Patient Composite Score | Compressed Score |
|---|---|
| 0-10 | 1 |
| 11-20 | 2 |
| 21-25 | 3 |
| 26-29 | 4 |
| 30-33 | 5 |
| 34-35 | 6 |
| 36-37 | 7 |
| 38-39 | 8 |
| 40 | 9 |
| 41+ | 10 |

FIG. 8

Table 4

| Population Score | # of Licensed Workers | # of Unlicensed Workers |
|---|---|---|
| 0-100 | 2 | 0 |
| 101-125 | 2 | 1 |
| 126-175 | 3 | 1 |
| 176-200 | 4 | 2 |
| 201-275 | 5 | 2 |
| 276-350 | 6 | 2 |
| 351-425 | 7 | 2 |
| 426-550 | 7 | 3 |
| 551+ | 8 | 3 |

Table 5

| Population Score | # of Licensed Workers | # of Unlicensed Workers |
|---|---|---|
| 0-100 | 2 | 0 |
| 101-125 | 2 | 1 |
| 126-175 | 3 | 1 |
| 176-200 | 4 | 2 |
| 201-275 | 5 | 2 |
| 276-325 | 6 | 3 |
| 326-375 | 6 | 4 |
| 376-400 | 7 | 5 |
| 401-475 | 7 | 5 |
| 476-500 | 8 | 5 |
| 501+ | 8 | 6 |

FIG. 10

Table 6

| Outpatient Indicator | Weighted Score |
|---|---|
| Patient Age | 2 if older than 55 years<br>1 if between 0 months and 18 years<br>0 if between 18-155 years |
| Time Since Check-In | 2 if more than 30 minutes<br>1 if between 15 and 30 minutes<br>0 if less than 15 minutes |
| Duration of Symptoms | 1 if more than 2 days<br>0 if less than 2 days |
| Active Infection | 2 if active infection<br>0 if no infection |
| Respiratory Problems | 2 if labored breathing<br>0 if no labored breathing |
| Blood Pressure | 3 if 4 standard deviations above/below normal<br>2 if 3 standard deviations above/below normal<br>1 if 2 standard deviations above/below normal<br>0 if 1 standard deviation above/below normal or normal |
| Body temperature | 3 if 4 standard deviations above/below normal<br>2 if 3 standard deviations above/below normal<br>1 if 2 standard deviations above/below normal<br>0 if 1 standard deviation above/below normal or normal |
| Medication | 1 if taking medications<br>0 if no medications |
| Medication level | 2 if taking more than 2 medications<br>1 if taking 1 medication<br>0 if taking no medication |
| Wounds | 2 if open wound or bleeding<br>0 if no open wound |
| Revisit | 4 if prior visit less than 2 days ago<br>2 if prior visit 3-7 days ago<br>1 if prior visit more than 1 week ago but less than 30 days ago<br>0 if prior visit more than 30 days ago |

FIG. 18

Table 7

| Population Score | # of Licensed Workers | # of Unlicensed Workers |
|---|---|---|
| 0-35 | 2 | 0 |
| 36-50 | 2 | 1 |
| 51-75 | 2 | 2 |
| 76-100 | 3 | 2 |
| 101-124 | 3 | 3 |
| 125-150 | 4 | 3 |
| 151-200 | 4 | 4 |
| 200+ | 5 | 4 |

FIG. 19

Table 8

| Resident Indicator | Weighted Score |
|---|---|
| Resident Age | 2 if older than 75 years |
| | 1 if between 55 years and 75 years |
| | 0 if between less than 55 years |
| Ambulatory | 1 if unable to walk |
| | 0 if able to walk |
| Dementia | 3 if late stage dementia |
| | 1 if early stage dementia |
| | 0 if no dementia |
| Active Infection | 1 if active infection |
| | 0 if no infection |
| Respiratory Problems | 1 if labored breathing |
| | 0 if no labored breathing |
| Blood Pressure | 4 if 4 standard deviations above/below normal |
| | 3 if 3 standard deviations above/below normal |
| | 2 if 2 standard deviations above/below normal |
| | 1 if 1 standard deviation above/below normal |
| | 0 if blood pressure normal |
| Parkinson's Disease | 2 if Parkinson's Disease |
| | 0 if no Parkinson's Disease |
| Medication | 1 if taking medications |
| | 0 if no medications |
| Medication level | 2 if taking 2 or more medications |
| | 1 if taking 1 medication |
| | 0 if taking no medication |
| Physical Therapy | 1 if physical therapy required |
| | 0 if no open physical therapy required |
| Joint replacement | 2 if joint replacement within 0-30 days |
| | 1 if join replacement within 30-60 days |
| | 0 if no joint replacement or joint replacement more than 60 days ago |
| DNR Order | 1 if no DNR order |
| | 0 if DNR order |

FIG. 20

Table 9

| Solider Indicator | Weighted Score |
|---|---|
| Head Trauma | 2 if head trauma<br>0 if no head trauma |
| Loss of Leg | 3 if loss of leg<br>0 if no limb loss |
| Shrapnel | 1 if shrapnel in body<br>0 if no shrapnel in body |
| Deceased | 1 if deceased<br>0 if alive |
| Gunshot wound | 1 if gunshot wound<br>0 if no gunshot wound |
| Blood Loss | 2 if blood loss<br>0 if no blood loss |
| Burns | 3 if $3^{rd}$ degree burns<br>2 if $2^{nd}$ degree burns<br>1 if $1^{st}$ degree burns<br>0 if no burns |
| Pain Medication | 1 if taking pain medication<br>0 if no pain medications |
| Ambulatory | 1 if cannot walk<br>0 if can walk |
| Conscious | 1 if unconscious<br>0 if conscious |
| Loss of arm or hand | 1 if loss of arm or hand<br>0 if no loss of arm or hand |
| Active Infection | 1 if active infection<br>0 if no active infection |
| Tissue Loss | 1 if tissue loss<br>0 if no tissue loss |
| Blast wounds | 2 if blast wounds<br>0 if no blast wounds |
| Internal organ injury | 1 if internal organ injury<br>0 if no internal organ injury |
| Airway management | 1 if airway management<br>0 if no airway management |
| Pneumothorax | 1 if pneumothorax<br>0 if no pneumothorax |

FIG. 21

Table 10

| Time | # RNs Baseline Scheduled | #RNs projected based on Acuity and workload indicator | # NAs Baseline Scheduled | #NAs projected based on Acuity and workload indicator |
|---|---|---|---|---|
| 0700 | 6 | 6 | 3 | 2 |
| 0800 | 6 | 6 | 3 | 2 |
| 0900 | 6 | 6 | 3 | 2 |
| 1000 | 6 | 5 | 3 | 2 |
| 1100 | 6 | 5 | 2 | 2 |
| 1200 | 6 | 5 | 2 | 2 |
| 1300 | 6 | 6 | 2 | 2 |
| 1400 | 6 | 6 | 2 | 3 |
| 1500 | 6 | 6 | 2 | 3 |
| 1600 | 5 | 6 | 1 | 3 |
| 1700 | 5 | 6 | 1 | 3 |
| 1800 | 5 | 6 | 1 | 2 |
| 1900 | 5 | 6 | 1 | 2 |
| 2000 | 5 | 6 | 1 | 1 |

| Assessment | |
|---|---|
| Neurological | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. Pediatrics- Level of Consciousness, fontenelle in infants, Pupils and Glasocoma score should be considered with the above assessment if data available. |
| Respiratory | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |

FIG. 29B

| | |
|---|---|
| Cardiovascular | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |
| Peripheral Vascular | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |

FIG. 29C

| | |
|---|---|
| Skin | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |
| Gastrointestinal | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |

FIG. 29D

| | |
|---|---|
| Genitourinary | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |
| | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |

FIG. 29E

| | |
|---|---|
| Psychosocial | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |
| Head and Neck | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3= assessment would be considered severely outside of normal range with 3 or more primary outlying elements/issues with 1 or more considered imminently life threatening based on data interpretation from clinical nursing, provider and other care givers assessment. Clinical assessment data should be considered in scoring but not duplicative based on other specific assessment indicators. |

FIG. 29F

| | | |
|---|---|---|
| | | score 0= assessment normal based on age and sex ; score 1 = assessment would be considered minimally outside of normal range with 1 primary outlying issue/element considered nonlife threatening ; score 2= assessment would be considered moderately outside of normal range with 2 primary outlying issues/elements with 1 potential life threatening; score 3=  assessment would be considered severely outside of normal range with 3 or more primary outlying elements/issues with 1 or more considered imminently life threatening based on data interpretation from clinical nursing, provider and other care givers assessment.   Clinical assessment data should be considered in scoring but not duplicative based on other specific assessment indicators. |
| Musculoskeletal | | |

| Sample Patient | Compressed Score | Intervention/Resource |
|---|---|---|
| A | 6 | |
| B | 5 | Medium |
| C | | Low |
| D | 3 | Low |

FIG. 30

| | Threshold | True Neg | False Pos | False Neg | True Pos |
|---|---|---|---|---|---|
| 1 | 0.01 | 140971 | 11927 | 80 | 1564 |
| 2 | 0.02 | 144941 | 7957 | 144 | 1500 |
| 3 | 0.03 | 146854 | 6044 | 173 | 1471 |
| 4 | 0.04 | 147957 | 4941 | 225 | 1419 |
| 5 | 0.05 | 148787 | 4111 | 262 | 1382 |
| 6 | 0.06 | 149344 | 3554 | 302 | 1342 |
| 7 | 0.07 | 149785 | 3113 | 332 | 1312 |
| 8 | 0.08 | 150169 | 2729 | 365 | 1279 |
| 9 | 0.09 | 150450 | 2448 | 398 | 1246 |
| 10 | 0.1 | 150694 | 2204 | 431 | 1213 |
| 11 | 0.25 | 152113 | 785 | 686 | 958 |
| 12 | 0.5 | 152657 | 241 | 969 | 675 |

GENERATING A MAP OF A MEDICAL FACILITY

PRIORITY APPLICATION

This application is a continuation application of U.S. patent application Ser. No. 14/209,439, filed Mar. 13, 2014, which claims priority to, and the benefit of, each of U.S. Provisional Application No. 61/896,980, filed on Oct. 29, 2013 and U.S. Provisional Application No. 61/785,407, filed on Mar. 14, 2013, the entire disclosure of each of which is herein incorporated by reference for all purposes.

TECHNOLOGICAL FIELD

Certain features, aspects and embodiments are directed to systems and methods for assessing staffing levels based on patient indicators and/or predicting patient outcomes using mortality risk values.

BACKGROUND

In many instances, determining the exact number of hospital staff needed to support a number of patients is based on census count, e.g., the total number of patients. This staffing can lead to an improper level of staff.

SUMMARY

In a first aspect, a method of assessing healthcare staffing levels for a health care unit is provided. In some embodiments, the method comprises determining a composite patient indicator score for each of a plurality of patients at a first period by scoring patient indicators using scores derived from empirical patient data, summing the composite patient indicator scores of the plurality of patients to provide a population score, and assigning a staffing level to the unit based on the summed population score.

In certain embodiments, the composite patient indicator score is determined by using a weighting factor scale range for each of the patient indicators, in which the weighting factor scale range is different for at least two of the patient indicators. In other embodiments, a patient indicator representative of a higher mortality risk has a greater range of values than a patient indicator representative of a lower mortality risk. In further embodiments, the method can include extracting the patient indicators from an electronic medical record. In some examples, the method can include determining a composite patient indicator score for each of the plurality of patients from the time of patient admission to the time of patient discharge or patient death. In other examples, the method can include weighting the population score. In other instances, the method can include comparing the weighted, population score of the plurality of patients to a weighted, population score of a different group of a plurality of patients. In certain examples, the method can include assigning staff to the plurality of patients and the different group of the plurality of patients based on the comparison step. In additional examples, the method can include determining a population score for each unit of a hospital. In some embodiments, the method can include redistributing a fixed number of staff using the determined population scores for each unit of the hospital. In certain embodiments, the method comprises graphically displaying each of the determined population scores for each unit of the hospital. In other embodiments, the graphically displaying step comprises color-coding the scores using at least a three level color coding scheme. In some embodiments, the method comprises predicting a future population score using the population score. In additional embodiments, at least one of the weighting factors is staggered over time in the predicted, future population score. In other embodiments, the determined, composite patient indicator scores are graphically displayed as one of three levels. In some examples, the determined, composite patient indicator scores are compressed on a 1-10 scale. In other examples, the method comprises determining the population score using patient indicators from each patient on a unit from the time of admission to the time of discharge of the patient. In some embodiments, the method comprises determining a patient indicator trend for each of the plurality of patients and summing the trend values for a first period. In additional embodiments, the method comprises determining a summed trend value at a second period, after the first period, and comparing the summed trend values of the first period and the second period. In certain instances, staffing levels are increased if the summed trend value of the second period increases by a threshold amount above the summed trend value of the first period. In other instances, the method comprises determining a summed reverse trend that is normalized to the admission time of each patient, e.g., is reversed back to time zero when the patient was admitted. In some examples, the method comprises entering patient indicators into an electronic medical record and automatically calculating the composite patient indicator score from the electronic medical record. In other examples, the method comprises automatically assigning a score to each of the patient indicators using scores derived from empirical patient data. In additional examples, the method comprises summing the automatically assigned scores to provide a patient indicator score for a particular patient. In certain embodiments, the method comprises compressing the summed, patient indicator score for the particular patient over a range of 1 to 10. In other embodiments, at least five of the patient indicators from Table 1 are used to determine the composite patient indicator score. In some embodiments, at least ten of the patient indicators from Table 1 are used to determine the composite patient indicator score. In additional embodiments, at least fifteen of the patient indicators from Table 1 are used to determine the composite patient indicator score. In other embodiments, at least twenty of the patient indicators from Table 1 are used to determine the composite patient indicator score. In some examples, the method can include unequally scoring the patient indicators using scores derived from empirical patient data, e.g., the scoring ranges for different indicators is different.

In another aspect, a method of assessing healthcare staffing levels comprising determining a composite patient indicator score for each of a plurality of patients by scoring patient indicators using scores derived from empirical patient data, compressing each of the determined, composite patient indicator scores between a selected range, summing the compressed, determined composite patient indicator scores of the plurality of patients to provide a compressed population score, and assigning a staffing level based on the compressed population score is disclosed.

In certain embodiments, the composite patient indicator score is determined by using a weighting factor scale range for each of the patient indicators, in which the weighting factor scale range is different for at least two of the patient indicators. In other embodiments, a patient indicator representative of a higher mortality risk has a greater range of values than a patient indicator representative of a lower mortality risk. In some examples, the method can include extracting the patient indicators from an electronic medical record. In other embodiments, the method can include determining a composite patient indicator score for each of the plurality of patients from the time of patient admission to the time of patient discharge or patient death. In further embodiments, the method can include weighting the compressed population score. In additional embodiments, the method can include comprising comparing the weighted, compressed population score of the plurality of patients to a weighted, compressed population score of a different group of a plurality of patients. In some examples, the method can include assigning staff to the plurality of patients and the different group of the plurality of patients based on the comparison step. In additional examples, the method can include determining a compressed population score for each unit of a hospital. In certain embodiments, the method can include redistributing a fixed number of staff using the determined compressed population scores for each unit of the hospital. In some examples, the method can include graphically displaying each of the determined compressed population scores for each unit of the hospital. In additional examples, the graphically displaying step comprises color-coding the scores using at least a three level color coding scheme. In further examples, the method can include predicting a future compressed population score using the compressed population score. In some embodiments, selected weighting factors are staggered over time in the predicted, future compressed population score. In additional embodiments, the compressed, determined composite patient indicator scores are graphically displayed at one of three levels. In some embodiments, the scores are compressed on a 1-10 scale. In other examples, the method can include determining the compressed population score for each patient on a unit from the time of admission to the time of discharge of the patient. In some embodiments, the method can include determining a patient indicator trend for each of the plurality of patients and summing the trend values for a first period. In certain examples, the method can include determining a summed trend value at a second period, after the first period, and comparing the summed trend values of the first period and the second period. In some instances, the staffing levels are increased if the summed trend value of the second period increases by a threshold amount over the summed trend value of the first period. In certain instances, the method can include determining a summed reverse trend that is normalized to the admission time of each patient. In other embodiments, the method can include entering patient indicators into an electronic medical record and automatically calculating the weighted patient indicator score from the electronic medical record. In certain embodiments, the method can include automatically assigning a score to each of the patient indicators using scores derived from empirical patient data. In additional embodiments, the method can include summing the automatically assigned scores to provide a patient indicator score for a particular patient. In certain examples, the method can include compressing the summed, patient indicator score for the particular patient over a range of 1 to 10. In other embodiments, at least five of the patient indicators from Table 1 are used to determine the composite patient indicator score. In some embodiments, at least ten of the patient indicators from Table 1 are used to determine the composite patient indicator score. In certain embodiments, at least fifteen of the patient indicators from Table 1 are used to determine the composite patient indicator score. In additional embodiments, at least twenty of the patient indicators from Table 1 are used to determine the composite patient indicator score. In certain examples, the method can include unequally scoring the patient indicators using the scores derived from empirical patient data.

In an additional aspect, a method of determining staffing levels in an ambulatory care setting is described. In certain examples, the method comprises determining a composite outpatient indicator score for each of a plurality of outpatients by scoring outpatient indicators using scores derived from empirical outpatient data, summing the outpatient indicator scores of the plurality of outpatients to provide a population score, and assigning a staffing level to the ambulatory care setting based on the summed outpatient population score.

In some embodiments, the outpatient indicator score is determined by using a weighting factor scale range for each of the outpatient indicators, in which the weighting factor scale range is different for at least two of the outpatient indicators. In other embodiments, an outpatient indicator representative of a higher mortality risk has a greater range of values than an outpatient indicator representative of a lower mortality risk. In further embodiments, the method can include extracting the outpatient indicators from an electronic medical record. In some examples, the method can include determining a composite outpatient indicator score for each of the plurality of outpatients from the time of patient triage to the time of patient discharge. In other embodiments, the method can include weighting the outpatient population score. In some examples, the method may include comparing the composite outpatient population score of the plurality of outpatients to a composite population score of a different group of a plurality of outpatients. In certain examples, the method may include assigning staff to the plurality of outpatients and the different group of the plurality of outpatients based on the comparison step. In other embodiments, the method may include determining a population score for each ambulatory care unit of a hospital. In certain examples, the method may include redistributing a fixed number of staff using the determined population scores for each ambulatory care unit of the hospital. In other embodiments, the method may include graphically displaying each of the determined population scores for each unit of the hospital. In some instances, the graphically displaying step comprises color-coding the population scores using at least a three level color coding scheme. In other examples, the method may include predicting a future outpatient population score using the outpatient population score. In some examples, selected weighting factors are staggered over time in the future population score. In other embodiments, the determined composite outpatient indicator scores are graphically displayed at one of three levels. In some embodiments, the composite outpatient scores are compressed on a 1-10 scale. In certain examples, the method can include determining the outpatient population score for each outpatient in an ambulatory care unit from the time of triage to the time of discharge of the outpatient. In other embodiments, the method can include determining an outpatient indicator trend for each of the plurality of outpatients and summing the trend values for a first period. In some instances, the method can include determining a summed trend value at a second period, after the first period, and comparing the summed trend values of the first period and the second period. In certain embodiments, staffing levels are increased if the summed trend value of the second period increases by a threshold amount over the summed trend value of the first period. In certain examples, the method can include determining a summed reverse trend that is normalized to the admission time of each outpatient. In some examples, the method can include entering outpatient indicators into an electronic medical record and automatically calculating the composite patient indicator score from the electronic medical record. In other embodiments, the method can include automatically assigning a score to each of the outpatient indicators using scores derived from empirical patient data. In additional embodiments, the method can include summing the automatically assigned scores to provide an outpatient indicator score for a particular outpatient. In further embodiments, the method can include compressing the summed, outpatient indicator score for the particular outpatient over a range of 1 to 10. In other examples, at least five of the outpatient indicators from Table 6 are used to determine the composite outpatient indicator score. In some examples, at least five of the outpatient indicators from Table 6 and at least five of the patient indicators from Table 1 are used to determine the composite outpatient indicator score. In certain examples, at least five of the outpatient indicators from Table 6 and at least ten of the patient indicators from Table 1 are used to determine the composite outpatient indicator score. In certain embodiments, at least five of the outpatient indicators from Table 6 and at least fifteen of the patient indicators from Table 1 are used to determine the composite outpatient indicator score. In other embodiments, the method can include unequally scoring the outpatient indicators using the scores derived from empirical patient data. In addition to the patients score post inpatient hospitalization or emergency visit may be originated in the outpatient office or clinic setting. Scores may be weighted and staggered based on outpatient office visit, new patient, number of disease processes, procedures and treatments performed in onsite in ambulatory setting, e.g., biopsy simple, moderate and complex, excision benign, excision non-benign, chemotherapy, radiation, laboratory review of biopsy required on site, surgical procedures. Clinical assessment review and the number of body systems out of Medications volume and amount, follow-up post intervention or treatment visits, examples might be colonoscopy, biopsy, stress test, medical devices monitoring/management remote and onsite. Number and type of procedures performed in the offices, lines, drains airways, infection status, physiological assessment, airway support, type of laboratory tests results, e.g., lactate, cholesterol, chemistry, white blood count etc, office discharge education.

In another aspect, a method of determining staffing levels in a nursing home comprising determining a composite resident indicator score for each of a plurality of nursing home residents by scoring resident indicators using scores derived from empirical resident data, summing the composite resident indicator scores of the plurality of residents to provide a resident population score, and assigning a staffing level to the nursing home based on the summed resident population score is provided.

In certain embodiments, the resident indicator score is determined by using a weighting factor scale range for each of the resident indicators, in which the weighting factor scale range is different for at least two of the resident indicators. In other embodiments, a resident indicator representative of a higher mortality risk has a greater range of values than a resident indicator representative of a lower mortality risk. In some examples, the method can include extracting the resident indicators from an electronic medical record. In additional examples, the method can include determining a composite resident indicator score for each of the plurality of residents from the time of patient triage to the time of patient discharge. In some embodiments, the method can include weighting the resident population score. In some examples, the method can include comparing the composite resident score of the plurality of residents to a composite population score of a different group of a plurality of residents. In additional examples, the method can include assigning staff to the plurality of residents and the different group of the plurality of residents based on the comparison step. In some embodiments, the method can include determining a population score for each resident unit of the nursing home. In certain examples, the method can include redistributing a fixed number of staff using the determined population scores for each resident unit of the nursing home. In some embodiments, the method can include graphically displaying each of the determined population scores for each unit of the nursing home. In certain examples, the graphically displaying step comprises color-coding the population scores using at least a three level color coding scheme. In other examples, the method can include predicting a future resident population score using the resident population score. In some embodiments, selected weighting factors are staggered over time in the future resident population score. In some instances, the determined composite resident indicator scores are graphically displayed at one of three levels. In other embodiments, the composite resident scores are compressed on a 1-10 scale. In some examples, the method can include determining the resident population score using each resident in a nursing home from the time of admission to the time of discharge or death. In additional examples, the method can include determining a resident indicator trend for each of the plurality of residents and summing the trend values for a first period. In some embodiments, the method can include determining a summed trend value at a second period, after the first period, and comparing the summed trend values of the first period and the second period. In certain embodiments, the staffing levels are increased if the summed trend value of the second period increases by a threshold amount over the summed trend value of the first period. In certain examples, the method can include determining a summed reverse trend that is normalized to the admission time of each resident. In certain embodiments, the method can include entering resident indicators into an electronic medical record and automatically calculating the composite resident indicator score from the electronic medical record. In other embodiments, the method can include automatically assigning a score to each of the resident indicators using scores derived from empirical patient data. In some examples, the method can include summing the automatically assigned scores to provide a resident indicator score for a particular resident. In certain examples, the method can include compressing the summed, resident indicator score for the particular outpatient over a range of 1 to 10. In some examples, at least five of the resident indicators from Table 8 are used to determine the composite resident indicator score. In other examples, at least five of the outpatient indicators from Table 8 and at least five of the patient indicators from Table 1 are used to determine the composite resident indicator score. In some examples, at least five of the outpatient indicators from Table 8 and at least ten of the patient indicators from Table 1 are used to determine the composite resident indicator score. In certain examples, at least five of the outpatient indicators from Table 8 and at least fifteen of the patient indicators from Table 1 are used to determine the composite resident indicator score. In some examples, the method can include unequally scoring the resident indicators using the scores derived from empirical patient data.

In another aspect, a method of determining staffing levels for military field hospitals comprising determining a composite soldier indicator score for each of a plurality of soldiers at a military field hospital by scoring soldier indicators using scores derived from empirical soldier data, summing the composite soldier indicator scores of the plurality of soldiers to provide a soldier population score, and assigning a staffing level to the military field hospital based on the soldier population score is disclosed.

In certain embodiments, the soldier indicator score is determined by using a weighting factor scale range for each of the soldier indicators, in which the weighting factor scale range is different for at least two of the soldier indicators. In some embodiments, a soldier indicator representative of a higher mortality risk has a greater range of values than a soldier indicator representative of a lower mortality risk.

In certain examples, the method comprises extracting the soldier indicators from an electronic medical record. In other examples, the method comprises determining a composite solider indicator score for each of the plurality of soldiers from the time of patient triage to the time of patient discharge. In additional examples, the method comprises weighting the soldier population score. In some embodiments, the method comprises comparing the composite soldier score of the plurality of soldiers to a composite population score of a different group of a plurality of soldiers. In further embodiments, the method comprises assigning staff to the plurality of soldiers and the different group of the plurality of soldiers based on the comparison step. In other examples, the method comprises determining a population score for each soldier of the military field hospital. In additional examples, the method comprises redistributing a fixed number of staff using the determined population scores for each military field hospital. In other embodiments, the method can include graphically displaying each of the determined population scores for each military field hospital. In other examples, the graphically displaying step comprises color-coding the population scores using at least a three level color coding scheme. In further examples, the method can include predicting a future soldier population score using the soldier population score. In additional examples, selected weighting factors are staggered over time m the future soldier population score. In further examples, the determined composite soldier indicator scores are graphically displayed at one of three levels. In some examples, the composite soldier scores are compressed on a 1-10 scale. In some embodiments, the method can include determining the soldier population score using each soldier in a military field hospital from the time of triage to the time of discharge or death. In additional embodiments, the method can include determining a soldier indicator trend for each of the plurality of soldiers and summing the trend values for a first period. In other examples, the method can include determining a summed trend value at a second period, after the first period, and comparing the summed trend values of the first period and the second period. In some examples, the staffing levels are increased if the summed trend value of the second period increases by a threshold amount over the summed trend value of the first period. In other examples, the method can include determining a summed reverse trend that is normalized to the admission time of each soldier. In certain examples, the method can include entering soldier indicators into an electronic medical record and automatically calculating the composite soldier indicator score from the electronic medical record. In other examples, the method can include automatically assigning a score to each of the soldier indicators using scores derived from empirical patient data. In some examples, the method can include summing the automatically assigned scores to provide a soldier indicator score for a particular soldier. In further examples, the method can include compressing the summed, soldier indicator score for the particular outpatient over a range of 1 to 10. In additional examples, at least five of the soldier indicators from Table 9 are used to determine the composite soldier indicator score. In other examples, at least five of the soldier indicators from Table 9 and at least five of the patient indicators from Table 1 are used to determine the composite soldier indicator score. In further examples, at least five of the soldier indicators from Table 9 and at least ten of the patient indicators from Table 1 are used to determine the composite soldier indicator score. In additional examples, at least five of the soldier indicators from Table 9 and at least fifteen of the patient indicators from Table 1 are used to determine the composite soldier indicator score. In some embodiments, the method can include unequally scoring the soldier indicators using the scores derived from empirical patient data.

In an additional aspect, a method of assigning a score to a patient comprising comparing patient indicators from a patient to a scoring table comprising unequally weighted scores based on empirical patient data, assigning a score from the scoring table to each of the patient indicators, and summing the assigned scores to provide a composite patient indicator score for the patient is provided.

In certain examples, the composite patient indicator score is determined by using a weighting factor scale range for each of the patient indicators, in which the weighting factor scale range is different for at least two of the patient indicators. In certain embodiments, a patient indicator representative of a higher mortality risk has a greater range of values than a patient indicator representative of a lower mortality risk. In other embodiments, the method can include extracting the patient indicators from an electronic medical record. In additional embodiments, the method can include assigning staff to the patient based on the composite patient indicator score. In other embodiments, the method can include graphically displaying the composite patient indicator score. In some examples, the graphically displaying step comprises color-coding the composite score using at least a three level color coding scheme. In some embodiments, the method can include predicting a future composite patient indicator score using the composite score. In certain examples, at least five of the patient indicators from Table 1 are used to determine the composite patient indicator score. In other examples, at least ten, at least fifteen or at least twenty of the patient indicators from Table 1 are used to determine the composite patient indicator score.

In another aspect, a method of assigning a population score to a patient population comprising comparing patient indicators from each of a plurality of patients to a scoring table comprising unequally weighted scores based on empirical patient data, assigning a score from the scoring table to each of the patient indicators from each of the plurality of patients, and summing the assigned scores to provide a composite population score for the patient population is disclosed.

In certain embodiments, the composite population score is determined by using a weighting factor scale range for each of the patient indicators, in which the weighting factor scale range is different for at least two of the patient indicators. In other embodiments, a patient indicator representative of a higher mortality risk has a greater range of values than a patient indicator representative of a lower mortality risk. In some embodiments, the method can include extracting the patient indicators from an electronic medical record. In certain examples, the method can include assigning staff to the patient population based on the composite population score. In some embodiments, the method can include graphically displaying the composite population score. In other embodiments, the graphically displaying step comprises color-coding the composite population score using at least a three level color coding scheme. In further examples, the method can include predicting a future composite population score using the composite population score. In other examples, at least five of the patient indicators from Table 1 are used to determine the composite population score. In some examples, at least ten, at least fifteen or at least twenty of the patient indicators from Table 1 are used to determine the composite population score.

In an additional aspect, a method of assigning a population score to outpatients of an ambulatory care setting, the method comprising comparing outpatient indicators from each of a plurality of patients to a scoring table comprising unequally weighted scores based on empirical patient data, assigning a score from the scoring table to each of the outpatient indicators from each of the plurality of outpatients, and summing the assigned scores to provide a composite population score for the outpatient population is described.

In some examples, the composite population score is determined by using a weighting factor scale range for each of the outpatient indicators, in which the weighting factor scale range is different for at least two of the outpatient indicators. In certain examples, an outpatient indicator representative of a higher mortality risk has a greater range of values than an outpatient indicator representative of a lower mortality risk. In other examples, the method can include extracting the outpatient indicators from an electronic medical record. In additional examples, the method can include assigning staff to the outpatient population based on the composite population score. In some embodiments, the method can include graphically displaying the composite population score. In other embodiments, the graphically displaying step comprises color-coding the composite population score using at least a three level color coding scheme. In some examples, the method can include predicting a future composite population score using the composite population score. In some examples, at least five of the outpatient indicators from Table 6 are used to determine the composite population score. In other examples, at least five of the outpatient indicators from Table 6 and at least five, at least ten, at least fifteen, or at least twenty of the patient indicators from Table 1 are used to determine the composite population score.

In another aspect, a method of assigning a population score to residents of a nursing home comprising comparing resident indicators from each of a plurality of residents to a scoring table comprising unequally weighted scores based on empirical patient data, assigning a score from the scoring table to each of the resident indicators from each of the plurality of residents, and summing the assigned scores to provide a composite population score for the residents is provided.

In certain examples, the composite population score is determined by using a weighting factor scale range for each of the resident indicators, in which the weighting factor scale range is different for at least two of the resident indicators. In certain embodiments, a resident indicator representative of a higher mortality risk has a greater range of values than a resident indicator representative of a lower mortality risk. In some examples, the method can include extracting the resident indicators from an electronic medical record. In additional examples, the method can include assigning staff to the resident population based on the composite population score. In further examples, the method can include graphically displaying the composite population score. In other embodiments, the graphically displaying step comprises color-coding the composite population score using at least a three level color coding scheme. In additional examples, the method can include comprising predicting a future composite population score using the composite population score. In further embodiments, at least five of the resident indicators from Table 8 are used to determine the composite population score. In additional embodiments, at least five of the resident indicators from Table 8 and at least five, at least ten, at least fifteen, or at least twenty of the patient indicators from Table 1 are used to determine the composite population score.

In an additional aspect, a method of assigning a population score to soldiers in a military field hospital comprising comparing soldier indicators from each of a plurality of soldiers to a scoring table comprising unequally weighted scores based on empirical patient data, assigning a score from the scoring table to each of the soldier indicators from each of the plurality of soldiers, and summing the assigned scores to provide a composite population score for the soldiers.

In certain embodiments, the composite population score is determined by using a weighting factor scale range for each of the soldier indicators, in which the weighting factor scale range is different for at least two of the soldier indicators. In other embodiments, a soldier indicator representative of a higher mortality risk has a greater range of values than a resident indicator representative of a lower mortality risk. In additional embodiments, the method can include extracting the soldier indicators from an electronic medical record. In some embodiments, the method can include assigning staff to the soldier population based on the composite population score. In further examples, the method can include graphically displaying the composite population score. In some embodiments, the graphically displaying step comprises color-coding the composite population score using at least a three level color coding scheme. In additional embodiments, the method can include predicting a future composite population score using the composite population score. In certain examples, at least five of the soldier indicators from Table 9 are used to determine the composite population score. In some examples, at least five of the soldier indicators from Table 9 and at least five, at least ten, at least fifteen, or at least twenty of the patient indicators from Table 1 are used to determine the composite population score.

In another aspect, a system for assessing healthcare staff levels comprising a first system configured to receive and store patient indicators from a plurality of patients during a first period, and a processor coupled to the first system and configured to retrieve the stored patient indicators during the first period and determine a summed population score for the first period by using scores derived from empirical patient data to determine a composite patient indicator score for each of a plurality of patients and summing the composite patient indicator scores of the plurality of patients to determine the composite population score is disclosed.

In some examples, the processor is further configured to retrieve stored patient indicators during a second period and determine a second, summed population score for the second period by determining a composite patient indicator score for each of a plurality of patients by scoring patient indicators using scores derived from empirical patient data and summing the composite patient indicator scores of the plurality of patients to provide a second composite population score. In certain examples, the processor is further configured to provide a population score trend as a function of time using the composite population score and the second, composite population score. In other examples, the processor comprises at least one lookup table to correlate the composite population score to a staffing level. In additional examples, the processor is configured to determine a plurality of composite population scores in real time. In some embodiments, the processor is configured to determine a composite population score for each unit of a hospital and assign staff to each unit of the hospital using the composite population scores. In additional embodiments, the processor comprises a scoring table to provide a score corresponding to each patient indicator. In some examples, the processor comprises a plurality of different scoring tables. In certain examples, the first system comprises an electronic medical record interface. In certain embodiments, the system can include a wireless receiver electrically coupled to the processor. In some examples, the system can include a wireless transmitter electrically coupled to the processor. In some embodiments, the first system is configured as a tablet device and the processor is wirelessly coupled to the tablet device. In other embodiments, the first system is configured as an electronic medical record database. In additional embodiments, the first system is located remote from the processor. In other embodiments, the first system is present at a residence of a patient and the processor is located remote from the residence of the patient. In some examples, the first system comprises a transmitter for sending patient indicators to the remote processor. In additional embodiments, the transmitter is a wireless transmitter. In other embodiments, the system can include a graphical device to display the composite population scores. In some examples, the system is configured to color code the composite population scores and display the color-coded scores on the graphical device. In additional examples, the first system comprises an interface configured to receive entry of patient indicators, in which the processor is configured to read the patient indicators entered into the interface and determine the composite population score by retrieving scores from a scoring table that correspond to the entered patient indicators and summing the retrieved scores.

In an additional aspect, a system for assessing healthcare staff levels in an ambulatory care setting, the system comprising a first system configured to receive and store outpatient indicators from a plurality of outpatients during a first period, and a processor coupled to the first system and configured to retrieve the stored outpatient indicators during the first period and determine a summed population score for the first period by using scores derived from empirical outpatient data to determine a composite outpatient indicator score for each of a plurality of outpatients and summing the composite outpatient indicator scores of the plurality of outpatients to determine the composite population score.

In certain embodiments, the processor is further configured to retrieve stored outpatient indicators during a second period and determine a second, summed population score for the second period by determining a composite outpatient indicator score for each of a plurality of outpatients by scoring outpatient indicators using scores derived from empirical patient data and summing the composite outpatient indicator scores of the plurality of outpatients to provide a second composite population score. In other embodiments, the processor is further configured to provide a population score trend as a function of time using the composite population score and the second, composite population score. In some embodiments, the processor comprises at least one lookup table to correlate the composite population score to a staffing level. In certain examples, the processor is configured to determine a plurality of composite population scores in real time. In additional examples, the processor is configured to determine a composite population score for each unit of an ambulatory care setting and assign staff to each unit using the composite population scores. In certain examples, the processor comprises a scoring table to provide a score corresponding to each outpatient indicator. In certain embodiments, the processor comprises a plurality of different scoring tables. In some embodiments, the first system comprises an electronic medical record interface. In additional embodiments, the system includes a wireless receiver electrically coupled to the processor. In further examples, the system includes a wireless transmitter electrically coupled to the processor. In some examples, the first system is configured as a tablet device and the processor is wirelessly coupled to the tablet device. In other examples, the first system is configured as an electronic medical record database. In additional examples, the first system is located remote from the processor. In some embodiments, the first system is present at an ambulatory care setting and the processor is located remote from the ambulatory care setting. In further examples, the first system comprises a transmitter for sending outpatient indicators to the remote processor. In additional examples, the transmitter is a wireless transmitter. In further embodiments, the system includes a graphical device to display the composite population scores. In some embodiments, the system is configured to color code the composite population scores and display the color-coded scores on the graphical device. In other embodiments, the first system comprises an interface configured to receive entry of outpatient indicators, in which the processor is configured to read the outpatient indicators entered into the interface and determine the composite population score by retrieving scores from a scoring table that correspond to the entered outpatient indicators and summing the retrieved scores.

In another aspect, a system for assessing healthcare staff levels in a nursing home comprising a first system configured to receive and store resident indicators from a plurality of residents during a first period, and a processor coupled to the first system and configured to retrieve the stored resident indicators during the first period and determine a summed population score for the first period by using scores derived from empirical resident data to determine a composite resident indicator score for each of a plurality of residents and summing the composite resident indicator scores of the plurality of residents to determine the composite population score is provided.

In certain embodiments, the processor is further configured to retrieve stored resident indicators during a second period and determine a second, summed population score for the second period by determining a composite resident indicator score for each of a plurality of residents by scoring resident indicators using scores derived from empirical resident data and summing the composite resident indicator scores of the plurality of residents to provide a second composite population score. In other embodiments, the processor is further configured to provide a population score trend as a function of time using the composite population score and the second, composite population score. In certain examples, the processor comprises at least one lookup table to correlate the composite population score to a staffing level. In some embodiments, the processor is configured to determine a plurality of composite population scores in real time. In certain examples, the processor is configured to determine a composite population score for each unit of a nursing home and assign staff to each unit using the composite population scores. In certain embodiments, the processor comprises a scoring table to provide a score corresponding to each resident indicator. In some examples, the processor comprises a plurality of different scoring tables. In certain examples, the first system comprises an electronic medical record interface. In other examples, the system can include a wireless receiver electrically coupled to the processor. In some embodiments, the system can include a wireless transmitter electrically coupled to the processor. In certain examples, the first system is configured as a tablet device and the processor is wirelessly coupled to the tablet device. In additional examples, the first system is configured as an electronic medical record database. In some embodiments, the first system is located remote from the processor. In additional embodiments, the first system is present at the nursing home and the processor is located remote from the nursing home. In some examples, the first system comprises a transmitter for sending resident indicators to the remote processor. In further examples, the transmitter is a wireless transmitter. In other embodiments, the system can include a graphical device to display the composite population scores. In some examples, the system is configured to color code the composite population scores and display the color-coded scores on the graphical device. In certain examples, the first system comprises an interface configured to receive entry of resident indicators, in which the processor is configured to read the resident indicators entered into the interface and determine the composite population score by retrieving scores from a scoring table that correspond to the entered resident indicators and summing the retrieved scores.

In an additional aspect, a system for assessing healthcare staff levels in a military field hospital comprising a first system configured to receive and store soldier indicators from a plurality of soldiers during a first period, and a processor coupled to the first system and configured to retrieve the stored solider indicators during the first period and determine a summed population score for the first period by using scores derived from empirical solider data to determine a composite soldier indicator score for each of a plurality of soldiers and summing the composite soldiers indicator scores of the plurality of soldiers to determine the composite population score is described.

In certain embodiments, the processor is further configured to retrieve stored soldier indicators during a second period and determine a second, summed population score for the second period by determining a composite soldier indicator score for each of a plurality of soldiers by scoring resident indicators using scores derived from empirical soldier data and summing the composite soldier indicator scores of the plurality of soldiers to provide a second composite population score. In other embodiments, the processor is further configured to provide a population score trend as a function of time using the composite population score and the second, composite population score. In some examples, the processor comprises at least one lookup table to correlate the composite population score to a staffing level. In other examples, the processor is configured to determine a plurality of composite population scores in real time. In additional examples, the processor is configured to determine a composite population score for each military field hospital in an area and assign staff to each hospital using the composite population scores. In some embodiments, the processor comprises a scoring table to provide a score corresponding to each soldier indicator. In other embodiments, the processor comprises a plurality of different scoring tables. In some examples, the first system comprises an electronic medical record interface. In other examples, the system includes a wireless receiver electrically coupled to the processor. In certain embodiments, the system includes a wireless transmitter electrically coupled to the processor. In other embodiments, the first system is configured as a tablet device and the processor is wirelessly coupled to the tablet device. In some examples, the first system is configured as an electronic medical record database. In additional embodiments, the first system is located remote from the processor. In other examples, the first system is present at the military field hospital and the processor is located remote from the military field hospital. In further examples, the first system comprises a transmitter for sending soldier indicators to the remote processor. In certain embodiments, the transmitter is a wireless transmitter. In additional embodiments, the system can include a graphical device to display the composite population scores. In further embodiments, the system is configured to color code the composite population scores and display the color-coded scores on the graphical device. In certain embodiments, the first system comprises an interface configured to receive entry of soldier indicators, in which the processor is configured to read the soldier indicators entered into the interface and determine the composite population score by retrieving scores from a scoring table that correspond to the entered soldier indicators and summing the retrieved scores.

In another aspect, a system for assessing the likelihood of readmission of a patient, the system comprising a processor configured to determine a composite patient indicator score from patient indicators during a period prior to patient discharge is provided.

In certain embodiments, the system includes a first system coupled to the processor, the first system configured to receive and store the patient indicators. In other embodiments, the period prior to discharge is at least 2 hours prior to discharge. In other embodiments, the determined, composite patient indicator score is compared to empirical patient data to determine the likelihood of readmission. In further embodiments, the empirical patient data comprises a lookup table that correlates average composite scores for a period with readmission likelihood. In certain examples, the system is configured to trigger an alert if the likelihood of admission exceeds a threshold value. In certain embodiments, the system is configured to determine a score trend between the period prior to discharge and discharge. In other examples, an increase in slope of the trend between the period prior to discharge and discharge triggers an alert. In additional examples, the system can include an empirical patient information system coupled to the processor. In other embodiments, the system can include a data entry system coupled to the processor.

Additional attributes, features, aspects, embodiments and configurations are described in more detail herein.

BRIEF DESCRIPTION OF THE FIGURES

Certain features, aspects and embodiments of the systems and methods are described with reference to the accompanying figures, in which:

FIGS. 1-4D include Table 1 which comprises patient indicators and weighted scores for each patient indicator, in accordance with certain examples;

FIGS. 5B-5F is a table of lab indicators and a corresponding scoring system, in accordance with certain examples;

FIG. 8 includes Tables 2 and 3, which are illustration of tables to correlate composite scores to compressed scores, in accordance with certain examples;

FIG. 10 includes Table 4 and 5, which are correlation tables for determining suitable staffing levels based on determined population scores, in accordance with certain examples;

FIG. 18 includes Table 6, which comprises outpatient indicators and corresponding scores, in accordance with certain examples;

FIG. 19 includes Table 7, which comprises a correlation table for outpatient population scores with staffing levels, in accordance with certain examples;

FIG. 20 includes Table 8, which comprises resident indicators and corresponding scores, in accordance with certain examples;

FIG. 21 includes Table 9, which comprises soldier indicators and corresponding scores, in accordance with certain examples;

FIG. 28 includes Table 10 which shows a suggested staffing level as a function of time and as a function of composite population scores (not shown), in accordance with certain examples;

FIGS. 29A-29F show assessment indicators and corresponding scores that may be used, in accordance with certain examples;

FIG. 30 shows a table of compressed scores and intervention/resources, in accordance with certain examples;

FIG. 31 is a table showing threshold values for mortality;

FIG. 33 is a listing showing the units, bed and scores; and

Figure 5A:
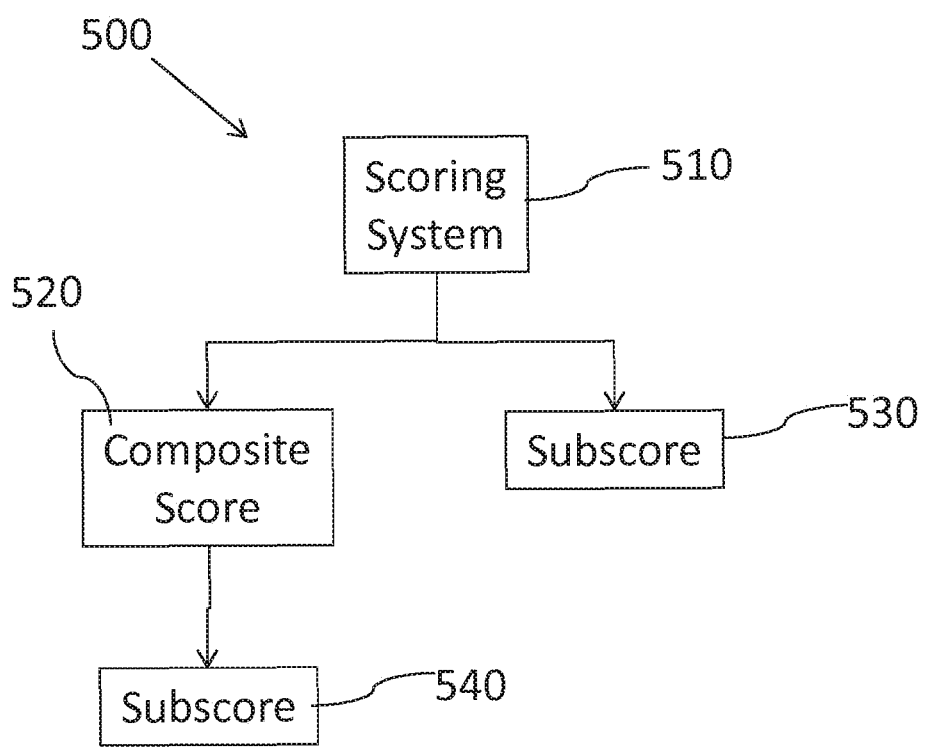
FIG. 5A is a schematic of a subscoring system, in accordance with certain examples.

It will be recognized by the person of ordinary skill in the art, given the benefit of this disclosure, that the components in the figures are not limiting and that additional components may also be included without departing from the spirit and scope of the technology described herein.

DETAILED DESCRIPTION

Certain features, aspects and embodiments described herein are directed to systems and methods that can be used to assess staffing levels in hospital units, nursing homes, ambulatory care units, military field hospitals and other setting where patients, outpatients or wounded individuals are being treated for one or more conditions. The term staffing levels, as used herein, refers to number of nurses, nursing assistants, physicians and/or other healthcare providers assigned to a particular unit, hospital or patient. If desired, the systems and methods can be used to distribute a fixed number of staff resources to various units within a care setting such that units with the most critical patients have higher staffing levels and units with less critical patients have lower staffing levels. In some instances, the systems and methods can be used to predict seasonal staffing levels based on empirical data from prior years, e.g., to predict suitable staffing levels during times of the year where influenza, norovirus or other conditions or diseases are likely to result in an increased patient population in a particular unit or care setting. Staffing levels may be adjusted by increasing the number of licensed professionals, e.g., doctors, nurses, etc., and/or increasing the number of non-licensed professionals, e.g., nursing assistants.

While certain illustrations are provided below with reference to indicators listed in the accompanying tables, the exact scoring used may be adjusted based on age, weight or patient population. For example, the scoring system selected may be tailored for pediatric care, neonatal intensive care, geriatrics, intensive care units, cardiac care units or other criteria. It may be desirable to use different scoring systems for certain patient populations to more heavily weight certain indicators than those same indicators would be weighted for a different population. In addition, where certain indicators may overlap or be measuring the same or a substantially similar condition or parameter, only one of those indicators may be used in the scoring system to avoid duplicate scoring of similar indicators. Each of the indicators described herein may have varying look back times in the source system, e.g., electronic medical record, medical device or other source. For example, a score of 3 for heart rate may be utilized until the next heart rate score is obtained and scored. As noted herein, the indicators can be used to assess the unique attributes of workload and/or care. In some embodiments, initial scores can be compared to subscores to assess whether early intervention may be warranted based on higher risk correlated to one or more subscores or whether the patient's age may indicate early intervention is desirable.

In certain embodiments, the scores and/or indicators can be used to predict or anticipate a patient population staffing level, e.g., based on mortality risk of the patient or patient population. For example, using the models described herein, e.g., a neural network model, or other suitable models, a predictive score can be generated and used to assess future staffing levels based on current patient data and/or indicators. It is a substantial attribute of the technology described herein that predictive scores can be provided to forecast staffing needs ahead of time to permit adjustment of staffing levels for a particular patient population or other group of individuals.

In some instances, the scoring methods implemented herein are based, at least in part, on empirical patient data. By basing the scoring methods on empirical patient data, different patient indicators are unequally weighted by providing larger score ranges for certain patient indicators and smaller score ranges for other patient indicators. In many existing scoring techniques, acuity scores are based on the same range, e.g., 0-4, such that unequal weighting is not possible. As described in more detail below, the unequal weighting of patient indicators can be used to assign a score to each of (or selected ones of) the patient indicators, sum the assigned scores for a particular patient, and, if desired, sum the assigned scores for all patients to assess staffing levels for a particular unit. In some instances, the individual summed scores for a particular patient are first compressed within a selected scale and then the compressed scores are summed to provide a compressed population score that is used to assess staffing levels. Illustrations of scoring, summing and compressing scores are provided in more detail below.

In certain embodiments, the methods, systems and devices described herein can be used to extract data from an electronic medical record or electronic device, receive data from an electronic medical record or an electronic device or combinations thereof. For example, electronic devices such as EKG monitors, ventricular assist devices, medication administration devices, ventilators, continuous renal therapy devices, hypothermia devices, and other medical equipment commonly used to monitor a patient and/or provide treatment can provide values that can be used in the systems and methods described herein.

In some instances, the systems and methods described herein can be used to correlate a patient indicator with a particular weighted score. In practice, the patient indicators would be generated by assessing a patient through nursing staff, supporting devices, e.g., heart monitors, blood pressure monitors, and other criteria. The patient indicators can be entered into a user interface (or otherwise received in some manner by the system) and used to assign a score to a particular patient indicator. For example, if a current patient's heart rate deviates from an average heart rate by 1 standard deviation, then a score of 1 may be assigned to that patient indicator. If the heart rate deviates by 2 standard deviations from the average, then a score of 2 may be assigned to the patient indicator. This scoring routine may be implemented for many other patient indicators commonly assessed by health care workers in a care setting.

Referring to FIGS. 1-4D, a representative list of patient indicators and weighted score ranges for a patient are listed. As noted herein, the particular score ranges for different patient indicators are different and are based, at least in part, on empirical patient data to provide more weighting to those indicators that are more likely to affect patient outcomes. It will be recognized by the person of ordinary skill in the art, given the benefit of this disclosure, that the particular patient indicators shown in FIGS. 1-4D are merely illustrative of the potential patient indicators that can be used. For example, the following additional indicators and score could be used: FIO2 (>=40% score=1), functional (1 person assist=score of 1, 2 person assist=score of 2, ambulated=score of 1, bed rest with bathroom privileges=score of 1, bed rest=score of 0), ICU or RN Patient Transport (score of 1 with a nurse or licensed health care provider, Score of 0 with non-licensed personnel), Incontinence (score of 1 if present), ventilator (score of 3 for high frequency, oscillator, bi-level or specialty vent, Score of 2 if ventilated, Score of 0 if non ventilated), Restraints (Score of 1 if present), Stool (score of 1 if stool present), urine occurrence (score of 1 if present; adjust for pediatric population), medication administration Record (score of 1 if MAR action from 1-216 performed within the hour, score of 0 if no MAR action performed), thermoregulation (score of 1 for warming or cooling), cardiac output device (score of 2 if present), or tracheostomy (score of 2 if present). In some embodiments, the patient indicators can be tailored or selected based on the particular unit, e.g., cardiac care unit, intensive care unit, ambulatory care unit, and examples of such tailored patient indicators are provided herein. Also as described herein, the exact number of patient indicators used to determine a summed score can vary from about five, ten, fifteen, twenty, twenty-five, thirty, thirty-five, forty, forty-five, fifty or more. Referring to FIG. 1, upon admission is patient is assigned a score of 3, which is staggered over time to 2, 1, and then 0. Various vital signs, lab tests, diagnostic tests, etc. may be performed by health care workers such as nurses and laboratory technicians. For example, the respiratory rate of the patient may be measured and a corresponding score is assigned by the system. A skin test, e.g., Braden score, may be performed. The Braden score generally measures the risk of pressure sores with a lower score indicative of higher risk. The particular Braden score can be correlated with a weighted score as shown in FIG. 1. A Morse score (indicative of a patient's likelihood of falling) can be assessed, and if the Morse score is less than 45 a score of 0 is assigned, otherwise a score of 1 is assigned for this patient indicator. A neurological assessment can be performed using many different techniques. For example, if a RASS (Richmond Agitation-Sedation Scale) is within an acceptable window, e.g., +2 to −2, then a score of zero is assigned, otherwise a score of 1 is assigned. If patient airways need to be drained then a score of 1 is assigned. If the patient has any wounds, then a score of 1 is assigned. If any medications are administered, then a score if 1 is assigned to this indicator. The volume of medications is also taken into account with more medications being taken receiving a higher score. In some instances, the type of medication being taken by the patient can be scored. For example, medication more commonly associated with acute conditions can receive a higher score than those associated with treating minor symptoms. Similarly, a weighted score can be assigned based on the volume of drips with a higher volume of drips receiving a higher score. If the patient is on isolation precautions, then a score of 1 is assigned. If the patient weight is greater than a threshold weight, e.g., 300 pounds, then a score of 2 is assigned. If the patient is above the normal weight, then a score of 1 is assigned. If the patient is of normal weight, then a score of 0 is assigned. If the patient receives blood products, then a score of 1 is assigned. For certain patient indicators, the particular score assigned is based on comparing the actual patient indicator to empirical, statistical values for that patient indicator. For example and referring to FIG. 2, a patient's blood pressure can be compared to a "normal" blood pressure range (based on age, race, etc.), and a particular score is assigned based on the deviation from the normal blood pressure range with a score of 4, 3, 2, 1 being assigned for 4 standard deviations, 3 standard deviations, 2 standard deviations, and 1 standard deviation, respectively, from the blood pressure normal range. Other patient indicators may also have weighted scores based on empirical statistical data. For example, heart rate, respiratory rate and body temperature may be scored by comparison to empirical, statistical data. Similarly (and referring to FIG. 1-4), carbon dioxide levels, lactic acid levels, blood oxygen levels, white blood cell count, hematocrit, international normalized ratios, creatine levels, mean corpuscular volume, red blood cell count, platelet count, iron levels, transferring levels, CD4%, LDH levels, HDL levels, LDL levels, levels of IgG, IgM or IgA, serum glucose levels or other patient indicators may be assigned a score by comparison of the actual values to empirical, statistical values. Referring again to FIG. 3, other indicators such as hypothermia, whether the patient is receiving certain therapies, e.g., dialysis, and the like may also be assigned a score. As shown in FIG. 3, hypothermia is a staggered score in that it decreases automatically over time from 3 to 2 to 1 to 0, and thus is weighted less over time in the overall summed score. Other staggered weighted scores may also be used in the systems and methods described herein.

In some embodiments, the empirical, statistical values used as reference values for assigning scores for a particular patient indicator may be based on the local population of patients that have been resident (or have visited) the particular care unit in prior years. In other instances, the empirical, statistical values may be based on combined data values from a similar population, e.g., similar race, age, ethnicity, etc., across a broader range of patients. In certain instances, a first score can be assigned based on empirical data from a local population, e.g., those resident in the care unit over the last year, and a second score can be assigned based on empirical data from a larger population, e.g., using data from patients in an entire state or country over the last year. The two scores can be compared, if desired, and either the higher or lower of the two scores can be used in the summed score. In some instances, the higher score is used to provide the summed score.

In certain embodiments, any one or more of the indicators shown in Table 1 (or other indicators described herein) can be grouped together to provide a subscore. For example, indicators or sub indicators can be combined for one, two or more physiological items and may also be reflected in a color coded icon, or trend real time or in timed intervals as described herein in reference to the composite scores or compressed scores. The icon may be displayed simultaneously with the composite score or the compressed score. A schematic of such a system is shown in FIG. 5A. The system 500 comprises a scoring system 510 that can provide a composite score 520 and optionally one or more subscores 530. In some instances, the composite score 520 may be first calculated and a subscore 540 may be calculated after the composite score 520 is calculated. In some instances, a plurality of subscores can be calculated and/or displayed along with, or in place of, the composite or compressed scores. For example, a heart rate score of 3, BP score of 1, Glascowa score of 0 to provide a subindicator composite score of 4 can be used. Certain scores may be adjusted in opposite directions proportional to the amount of support. For example, a table of lab results and corresponding scores is shown in FIGS. 5B-5F. Any one or more of these values can be used to calculate a composite score or a subscore or combinations thereof.

Figure 6:
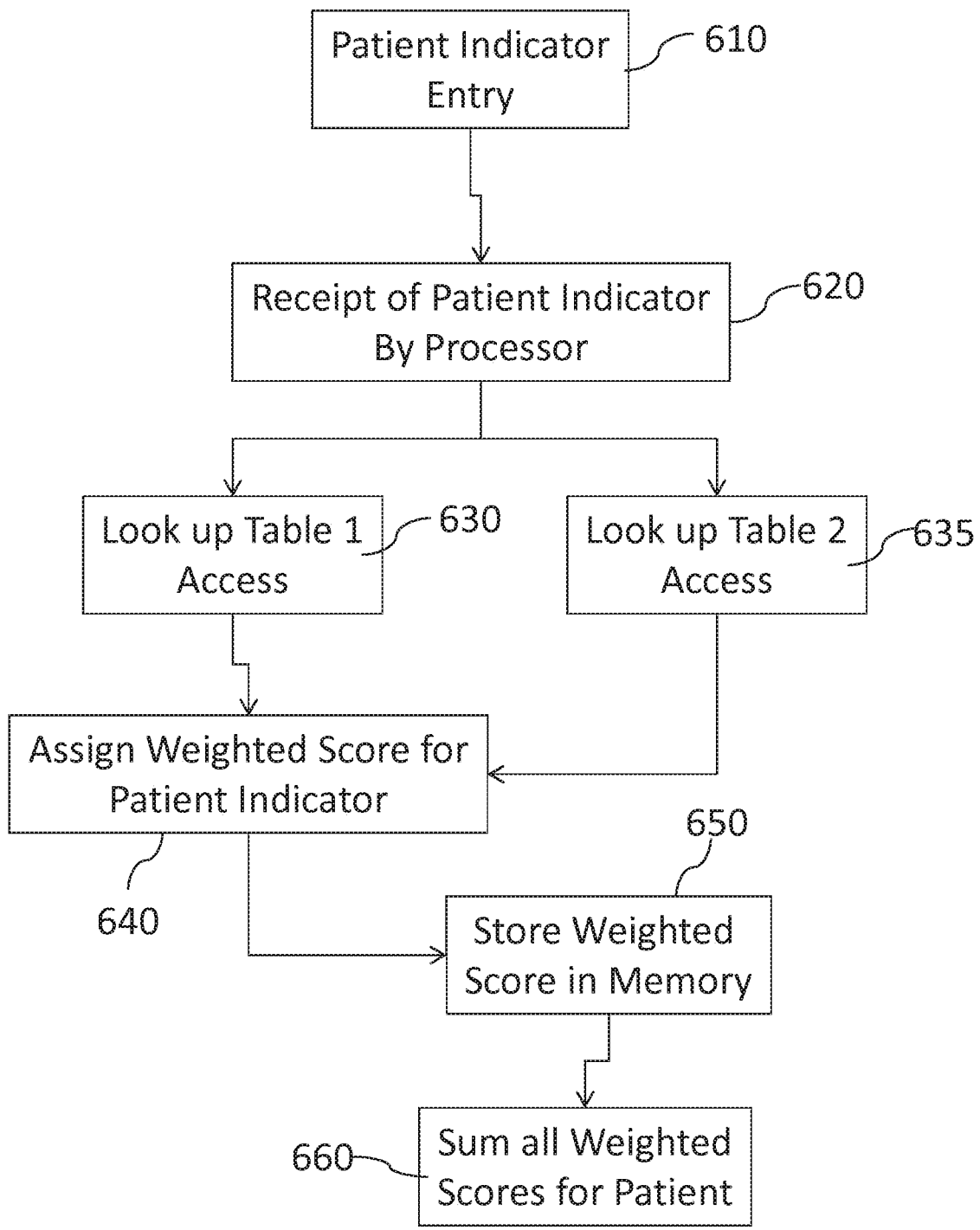
FIG. 6 is a schematic of a method for determining weighted scores, in accordance with certain examples.

In certain examples, as health care workers assess patient indicators, the patient indicators may automatically assigned a weighted score in real time by the system. For example and referring to FIG. 6, as a health care workers enters patient indicator data into a system at a step 610, a processor receives the patient indicators at a step 620 and accesses a look up table at a step 630 to assign a weighted score to the patient indicator at a step 640. As noted herein, if desired, the processor may access more than a single lookup table. For example, a second lookup table may be present and include empirical statistical data from a different population that the empirical data from the first lookup table. The processor can access the second lookup table at step 635 and assign a weighted score based on the values in the second lookup table. If desired, the scores can be compared (not shown), both scores can be stored at step 650 or the higher score from the two different lookup tables can be stored in step 650. This scoring process typically would continue in real time as patient indicators are entered into the system. The weighted score can be stored in memory (or in the processor) at a step 650 until no additional patient indicators are received after a first period, e.g., within a processing period. In some instances, the processing period may end when a health care worker leaves the patient room. For example, the health care worker may include or be wearing an RFID tag or other electronic device that can sense when the health care workers has left the room and when patient data entry has terminated. Where a healthcare provider utilizes telemedicine to diagnose and/or treat a patient, the amount of time the provider is present during the treatment process can be recorded. In other instances, a time-out period of 1-5 minutes from last data entry may be used as the processing period. The weighted scores in the memory can then be summed to provide a composite patient score at step 660. If desired, an RFID chip or other device can be located on a device used by the workers, and as workers pass by a room, the particular score of a patient in the room can be read by the device and displayed.

Figure 7:
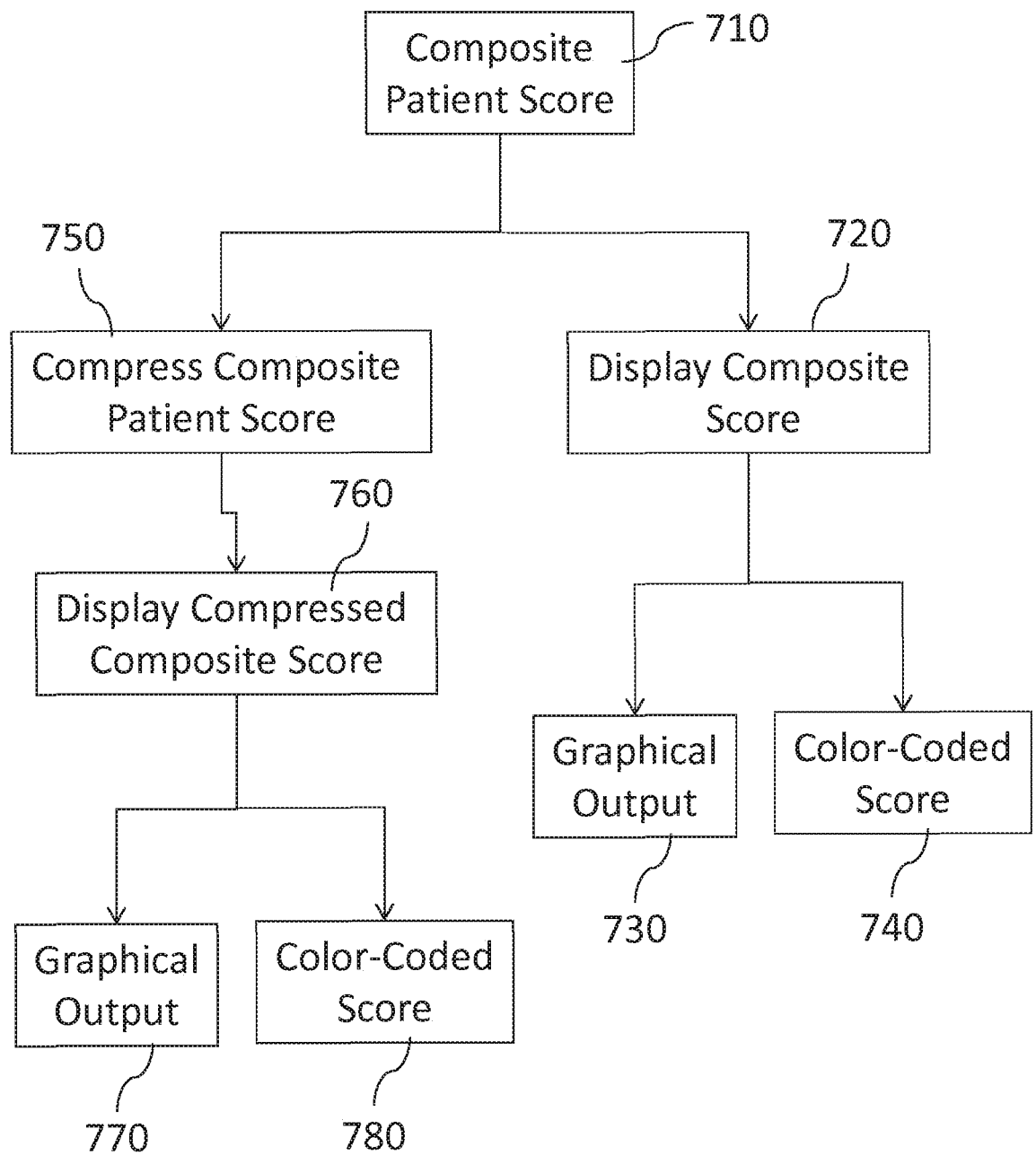
FIG. 7 is a schematic of a method for determining composite scores, in accordance with certain examples.

In certain embodiments, the composite score of the patient can be displayed, scaled or otherwise outputted in many different forms. For example and referring to FIG. 7, the composite patient score 710 may be displayed in real time at a step 720. For example, the composite score can be displaced in the form of a chart or graph at a step 730 so that hospital care workers (or hospital administrators) can monitor patient scores in real time. In other instances, the composite score can be color-coded, e.g., red, yellow, green, at a step 740 based on three levels to provide a visual indicator of the patient status in real time. Alternatively, the composite patient score can be compressed at a step 750 such that the actual scores fall within a desired numerical range, e.g., 1-5 or 1-10. Compression of the scores may provide for easier viewing and/or grouping of the scores. The compressed scores can be displayed graphically at step 770 or color-coded at step 780 similar to the color-coding scheme described in reference to step 740. In addition, different color-coding schemes may be selected for the compressed score and the uncompressed score.

In certain examples and referring to FIG. 8, a patient's composite score can be compressed by comparing the composite patient score to a compressed scoring table and extracting the value in the compressed scoring table that corresponds to the composite patient score. For example and referring to Table 2 in FIG. 8, if a patient's composite score is between 0-5 then a compressed score of 1 may be assigned. If a patient's composite score is between 6-10 then a compressed score of 2 is assigned. Other compressed score values as shown in Table 2 of FIG. 8 may be assigned based on the particular composite patient score. If desired, the compressed table may take into account that patients with higher scores are in more need of care than those with lower scores. As such, a compressed score can be produced where the higher composite scores are grouped over a small range and lower composite scores are grouped over a broader range. For example and referring to Table 3 in FIG. 8, composite scores from 0-10 are provided a compressed score of 1, and composite scores from 11-20 are provided a compressed score of 2. As the composite score values increase further, the range of composite scores that correspond to a particular compressed score is reduced. For example, the composite score range is reduced from 4 to 3 as the compressed score goes from 4 to 5, respectively. The compressed score of 8 corresponds to a composite score of 38-39 (range of 2 score unit), whereas the compressed score of 9 corresponds to a composite score of 40 (range of 1 score unit). By weighting the compressed score toward the higher end of the composite score range, those patients more in need of treatment can be easily identified. While the compressed scores shown in FIG. 8 range from 1-10, other ranges such as 0-10, 0-9, 0-8, 0-7, 0-6, 0-5 or any values in between these illustrative values may be used instead. If desired, the compressed scores may be color-coded, e.g., rainbow coded, with red colors indicative of higher compresses scores and violet color indicative of a lower compressed score. Displaying compressed scores by color-coding provides a rapid visual indicator.

Figure 9:
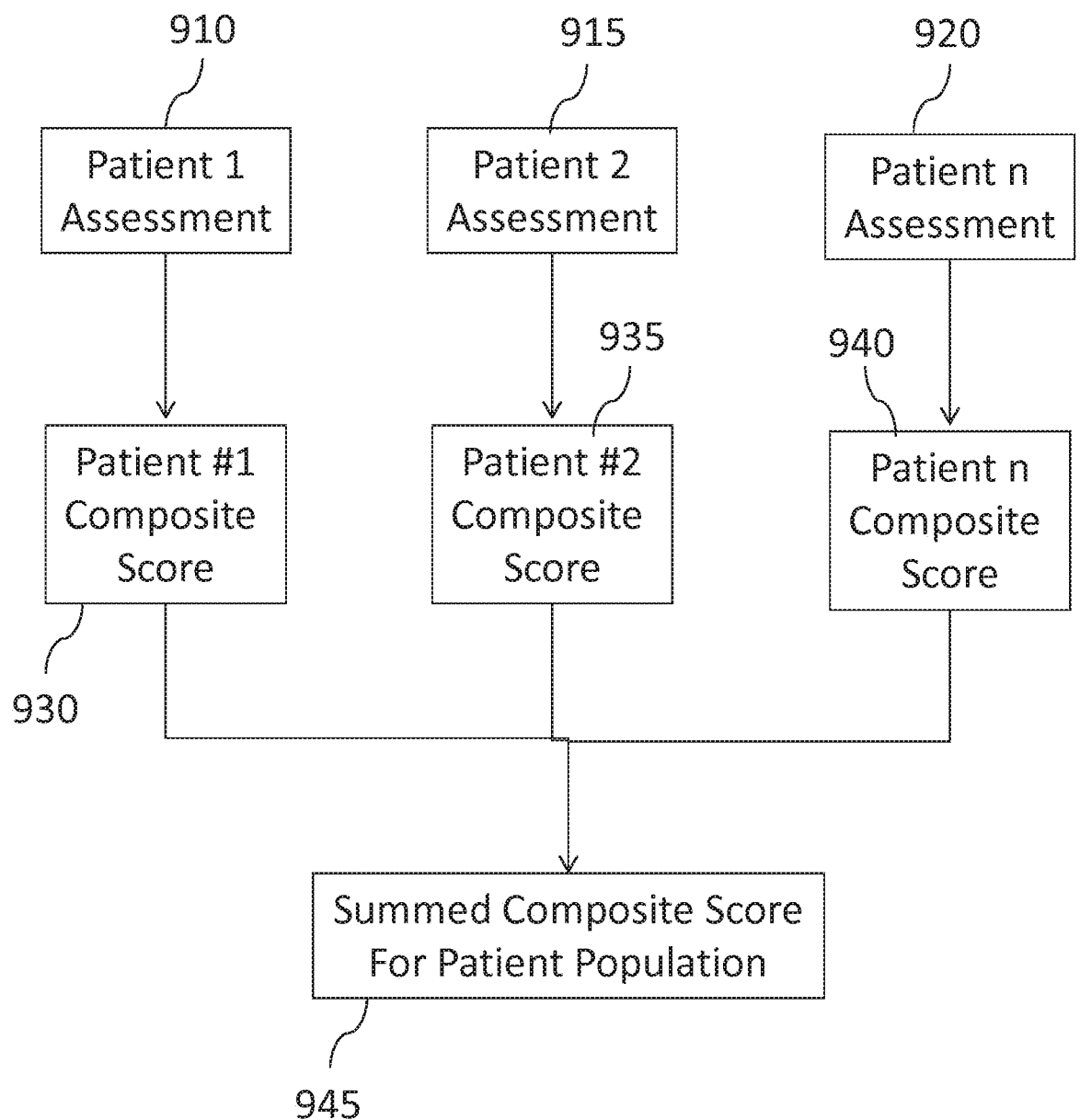
FIG. 9 is a schematic of a process to determine summed composite scores for a patient population, in accordance with certain examples.

In certain embodiments, the composite scores of each patient (either uncompressed composite scores or compressed composite scores) within a particular unit or care setting can be summed together to provide a population score. A schematic of this process is shown in FIG. 9. Patients 1, 2 . . . n are each assessed at steps 910, 915 and 920, respectively, by one or more health care providers. A composite score for patients 1, 2 . . . n is determined at steps 930, 935 and 940, respectively, by the system. The composite scores for all patients within the particular unit are added together at step 950 to provide a population score.

In certain examples, the population score for a particular unit can be correlated to a staffing lookup table to assess the number and/or level of staff needed or desired for a particular patient population. For example and referring to FIG. 10, population score values can be correlated to the number of licensed care workers (e.g., nurses, physicians, etc.) and the number of unlicensed care workers needed to care for a particular patient population. In Table 4 of FIG. 10, if the patient population score is 220, then 5 licensed healthcare workers and 2 unlicensed healthcare workers are recommended staffing levels. If the patient population score is 365, then 7 licensed healthcare workers and 2 unlicensed healthcare workers are recommended staffing levels. The exact level of staff recommend may vary depending on the particular unit where the population score originates. For example and referring to Table 5, if the particular unit generally includes more critically ill patients, then the staffing lookup table can be adjusted accordingly to provide for additional workers for that unit. For a patient population score of 365, Table 5 provides that 10 total workers (6 licensed workers and 4 unlicensed workers) would be adequate staffing, whereas Table 4 would provide for only 9 total workers. As noted in more detail below, depending on the particular care setting, e.g., ambulatory care, nursing home, military field hospital, etc. that exact numbers of licensed and unlicensed workers for a particular population score will vary.

Figure 11:
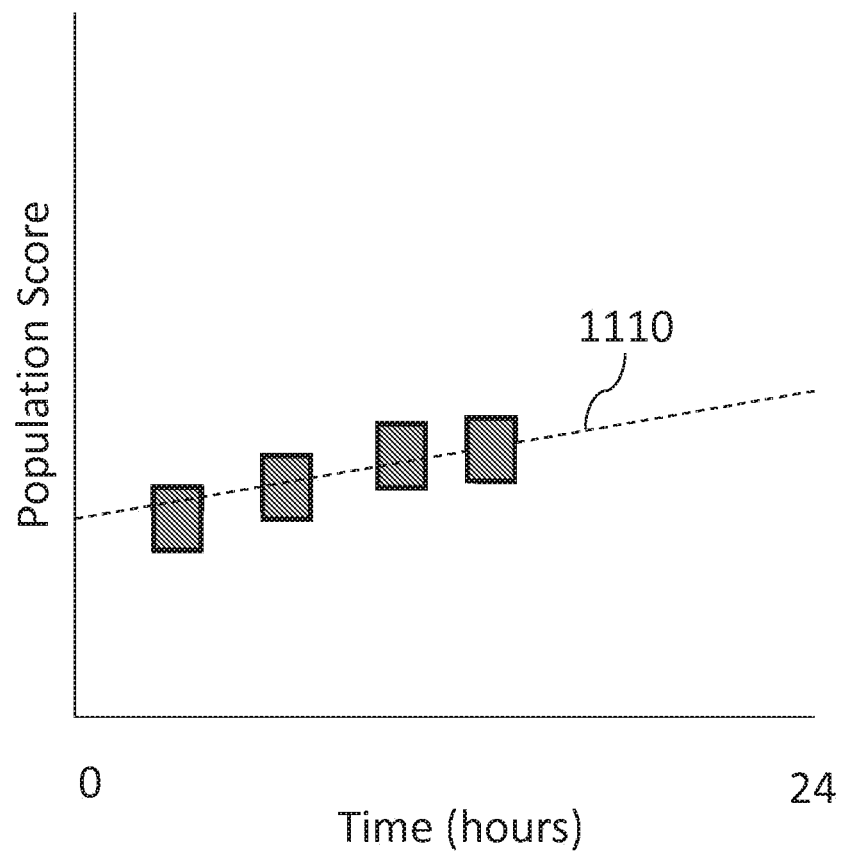
FIG. 11 is a graph of population score versus time that can be used to predict future population scores.
Figure 12:
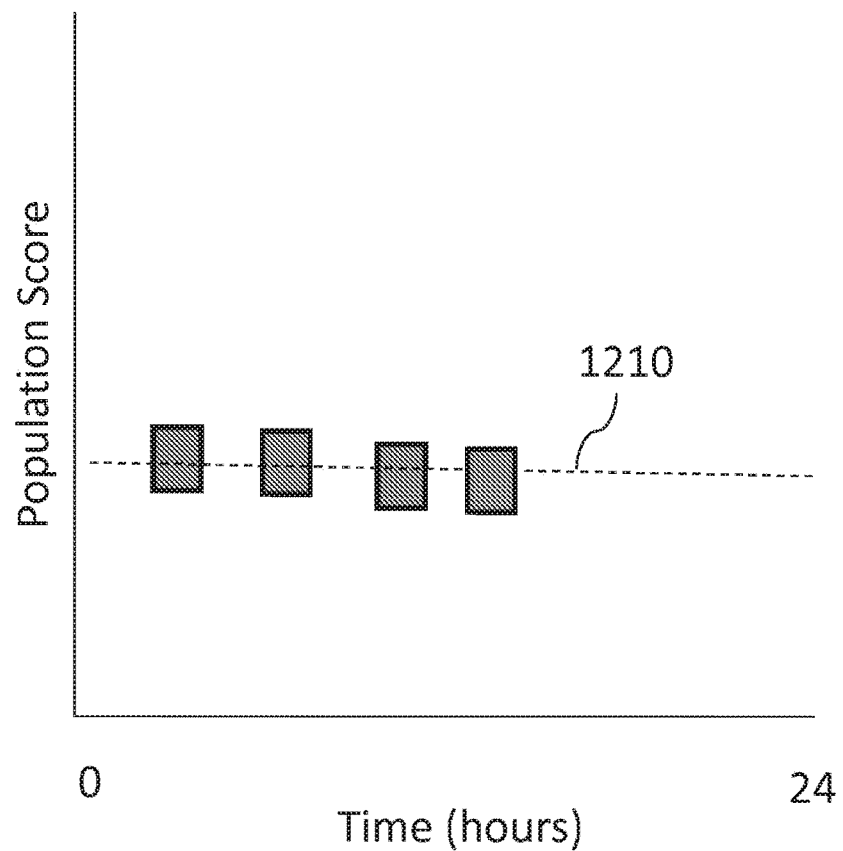
FIG. 12 is another graph of population score versus time that can be used to predict future population scores.

In certain embodiments, the population scores of a particular unit can be monitored over time and projected outward to assess whether additional staffing levels may be needed at a later time. Referring to FIG. 11, four population scores are shown as squares. A trend may be established to predict whether or not additional staffing levels may be needed at a future time. For example, a trend line 1110 has been fitted to the population scores to predict the potential population score at a later time. If the slope of the trend line 1110 exceed a certain value, then the system may be configured to increase staffing levels to the next level above a current level, e.g., to increase the staffing levels to the level based on the next higher population score interval. Similarly, if the trend line demonstrates a negative slope as shown in FIG. 12, then staffing levels may be maintained, or if the slope trend line decreases by a certain amount, staffing levels may be reduced. It will be recognized by the person of ordinary skill in the art, given the benefit of this disclosure that the exact equation used to provide the trend line need not be linear. In some embodiments, polynomial, logarithmic or other non-linear equations can be fit to the population scores to permit trend monitoring. In addition, it may be desirable to determine trends in compressed population scores instead of, or in addition to, the trends determined using uncompressed population scores.

Figure 13:
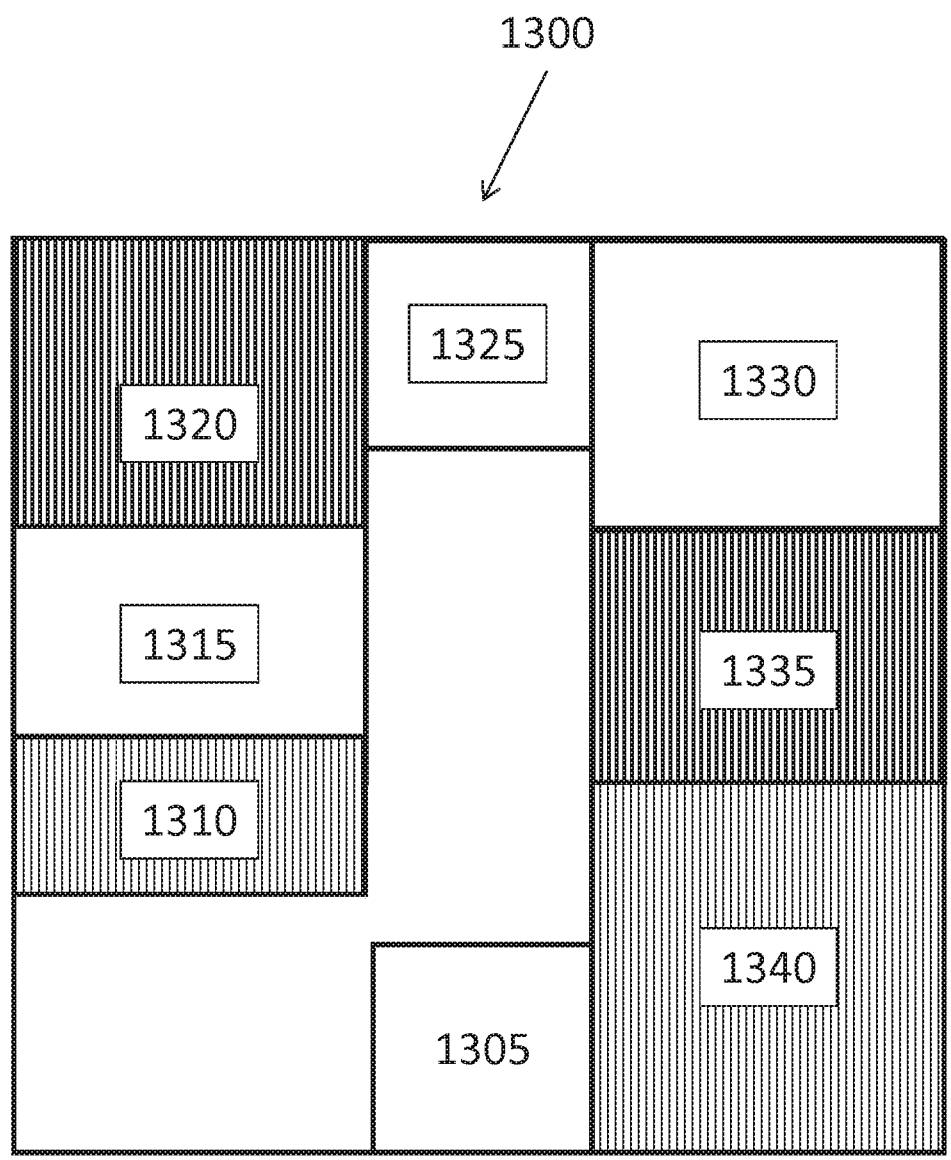
FIG. 13 is a graphical illustration representing a care unit with scores for each room displayed according to line shading, in accordance with certain examples.
Figure 14:
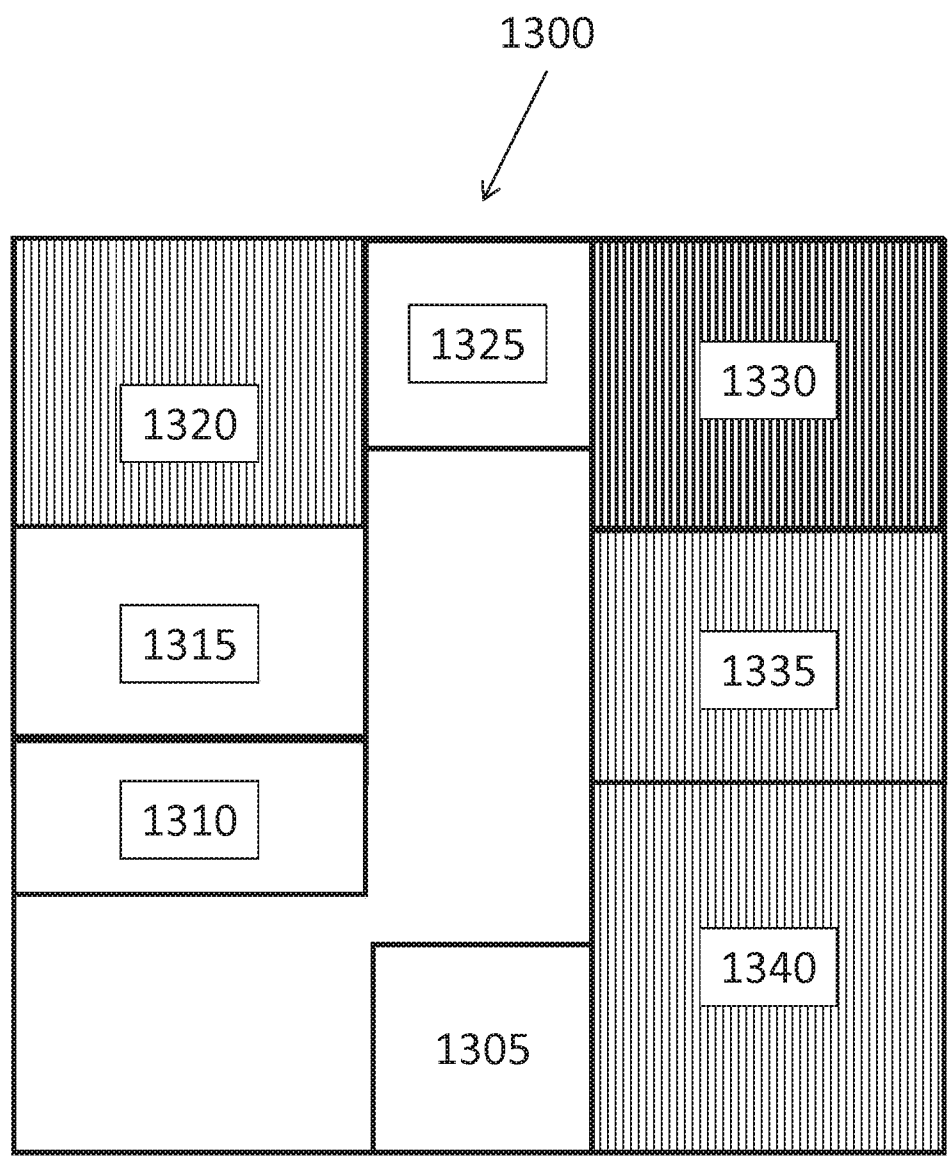
FIG. 14 is a graphical illustration of FIG. 13 at a second time, in accordance with certain examples.

In some examples, the systems described herein can be configured to provide a graphical representation of each patient's composite score to provide a visual indicator of the status of that particular patient. Referring to FIG. 13, a schematic of a care unit 1300 showing rooms 1310-1340 and a nurse station 1305 is shown. A three-level coding scheme has been implemented and represented for illustration purpose by lines with decreased line reflecting a higher composite score for that particular patient. In practice, a three-level color coding scheme, e.g., red, yellow, green, can be implemented such that patients with higher composite scores can be coded red and patients with lower composite scores can be coded green. Patients in rooms 1320 and 1335 have the highest composite scores, followed by patients in rooms 1310 and 1340. Patients in rooms 1315, 1325 and 1330 have the lowest composite scores. The composite scores can be displayed in real time and may change from minute-to-minute or hour-to-hour or other desired frequency. For example and referring to FIG. 14, the same unit 1300 as shown in FIG. 13 is shown at a time 4 hours later from that shown in FIG. 13. At this second period, patients in rooms 1310, 1315 and 1325 have the lowest composite scores. The composite score for the patient in room 1310 has decreased to the level where no shading is present. In contrast, the composite score for the patient in room 1330 has increased to the point where substantial shading is now present, indicating a higher composite score level than that shown in FIG. 13. The composite score for the patients in rooms 1320 and 1334 have decreased to the extent that they are now coded in the mid-range. As the system calculates the patient composite scores in real-time, the display can be adjusted accordingly so care givers have instant feedback regarding patients in a particular unit.

Figure 15:
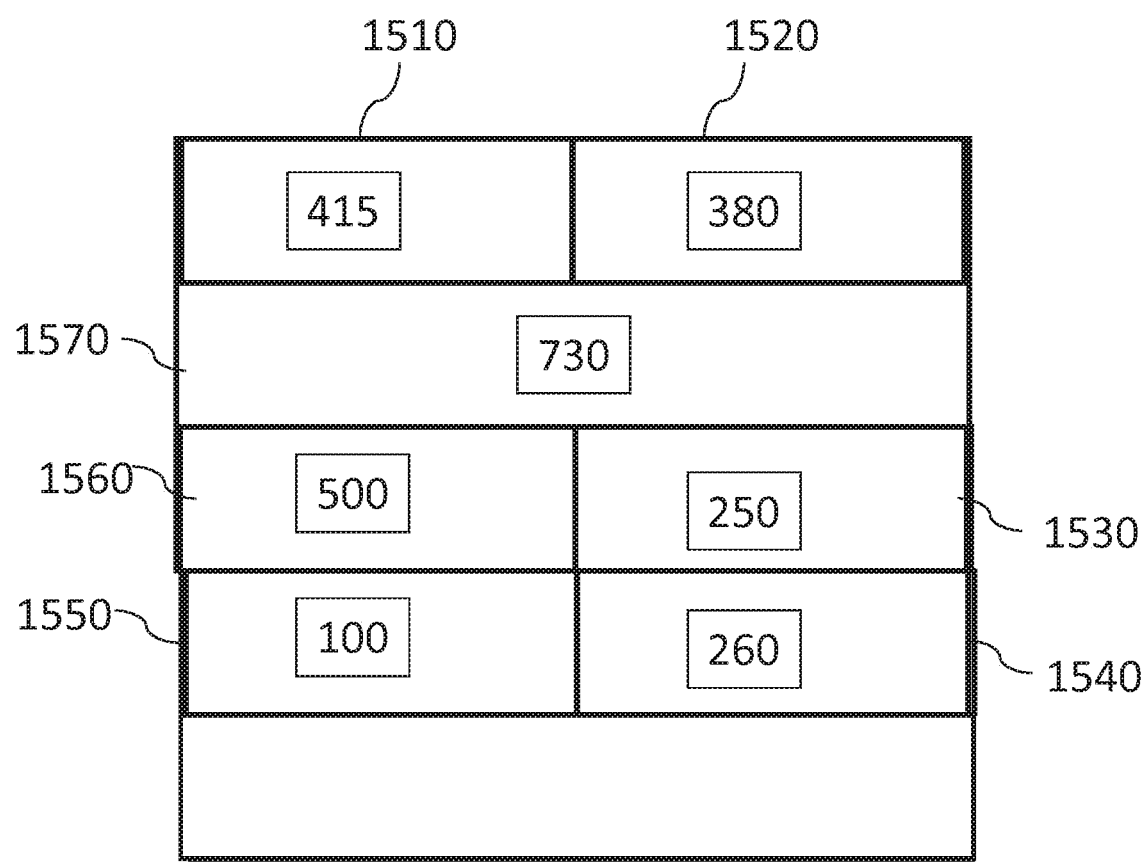
FIG. 15 is a graphical representation of different care units in a five floor tertiary care unit with the scores for each unit displayed, in accordance with certain examples.

In certain examples, a similar coding scheme may be utilized for assessing staffing levels within a hospital or other care setting. Referring to FIG. 15, a side view of a hospital 1500 is schematically represented with floors of different units corresponding to reference numerals 1510-1570. In this example, a five-floor tertiary care center is shown with 7 different units. The population score from each of the units 1510-1570 can be displayed as an actual number in the particular graphical representation (as shown in FIG. 15). For example, unit 1570 has a population score corresponding to a value of 730, whereas unit 1550 has a population score corresponding to a value of 100. Rather than the display of the exact population score, the system may be configured to implement a three-level color coding scheme (or other coding scheme) to provide for rapid visual feedback. In addition, the system may be configured to compare the actual staffing on a particular unit to the suggested level of staffing on a particular unit and send an alert to an administrator if the values differ or if the values differ by a certain level. Similarly, the system may be configured to generate an alert if one or more units changes from one coding level, e.g., yellow, to another coding level, e.g., red, to permit an administrator to adjust staffing needs accordingly. In some embodiments, a system similar to that shown in FIG. 15 can be used to distribute a fixed number of staff within a care system. For example, if the scores of unit 1550 remain low, e.g., 100 or less, than it may be desirable to redistribute one or more workers from unit 1550 to unit 1570 where the score is higher. In this manner, a fixed number of healthcare workers can be distributed in the most effective way to provide improved patient care.

Figure 16:
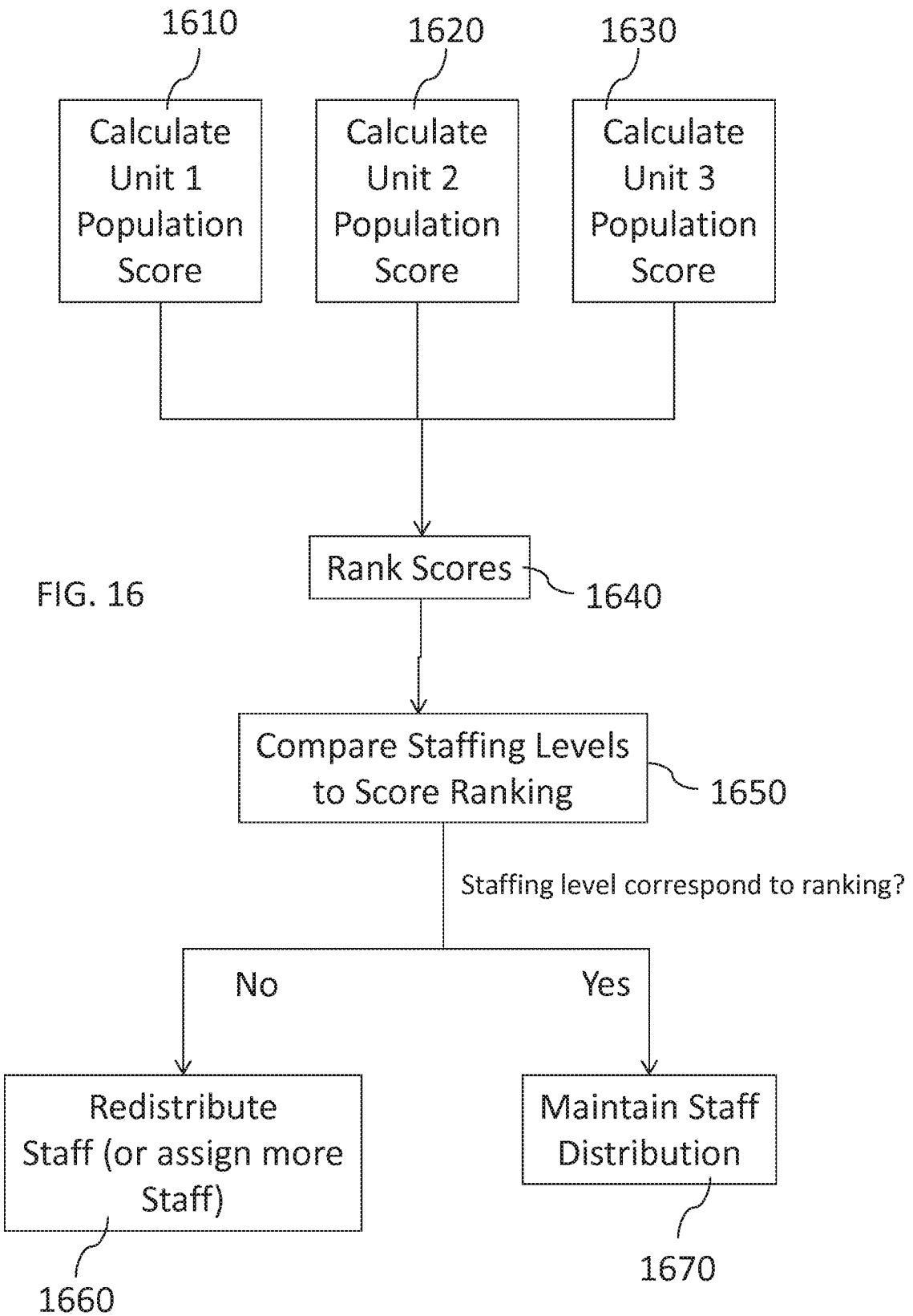
FIG. 16 is a schematic of a method that ranks scores for different units and compares the rank to the staffing levels, in accordance with certain examples.

In some examples, the scores of various units may be continuously compared with each other and staffing can be assigned based on score ranking. For example and referring to FIG. 16, population scores for three units can be calculated at steps 1610, 1620 and 1630. The calculated population scores can be ranked at step 1640, e.g., ranked high to low, and the level of staffing for each rank can be compared to the score rank. In most instances, scores ranked higher would be expected to have larger staff numbers. If the particular staffing level at a lower rank exceeds a staffing level at a higher rank, then either staff may be redistributed to the unit with the higher score ranking at step 1660 or more staff may be assigned to units with higher score rankings. If the staffing levels are consistent with the corresponding score rankings, then the staff distribution (and/or levels) can be maintained. The unit scoring and ranking may be performed in real-time or at a selected frequency, e.g., hourly, every 2 hours, every 3 hours, every 4 hours, etc., to assess staffing levels.

Figure 17A:
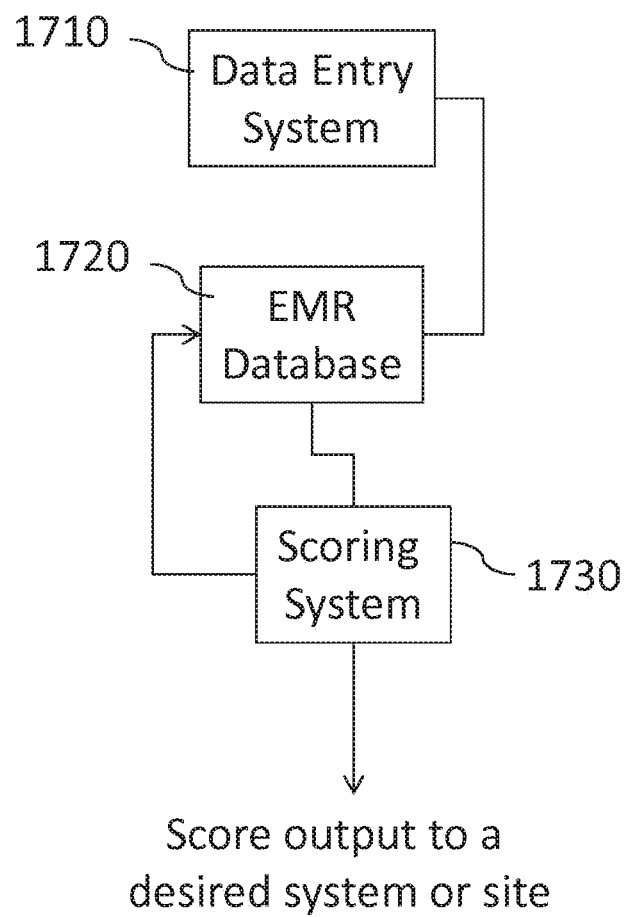
FIG. 17A is schematic of a system for scoring that can access an electronic medical record, in accordance with certain examples.

In certain embodiments, the methods and systems described herein may be configured to work with one or more electronic medical records, electronic devices, electronic medical record databases or combinations thereof. For example, the systems described herein can receive patient indicators listed on an electronic medical record (or directly from an electronic device), extract desired patient indicators, determine a weighted, composite score for the patient based on the medical records and display or otherwise output the weighted, composite score. If desired, the weighted, composite score determined from electronic medical records of all patients in a unit may be determined and summed to provide a population score as described herein. In one configuration of a system, the system may be separate from an electronic medical record system as shown in FIG. 17A. The system 1700 includes a data entry system 1710 coupled to an electronic medical record (EMR) database 1720. The EMR database is coupled to a scoring system 1630 which can provide composite scores, population scores or both as described herein. While not shown, each of the systems 1710, 1720 and 1730 typically includes a processor and one or more memory units to permit receipt of patient indicators and processing of them in a desired manner. The determined scores can be outputted to a desired system or site and may optionally be provided back to the EMR database 1720 for storage and/or tracking. In some examples, the data entry system 1710 may be configured such that health care workers entering patient indicators select from a menu or other interface options that correspond to the particular scores, e.g., select a particular respiratory rate for the patient. In other instances, actual parameters are entered into the data entry system 1710, and the scoring system 1730 can read those parameters from the EMR database 1730 and convert them into a usable score. In other instances, the scoring system 1730 may be configured to mine the EMR database 1720 by searching for keywords in the EMR and using the identified keywords to determine a score. While the data entry system 1710, the EMR database 1720 and the scoring system 1730 are shown as being linked in FIG. 17A, they may be linked wirelessly, in a wired manner or in any other manner that permits data or values from one system to be transmitted to another system. If desired, the data entry system 1720 and EMR database 1720 may be combined into a single system. Similarly, the scoring system 1730 may be combined with either the data entry system 1710 or the EMR database 1720 such that a single processor can be used for multiple different systems. In some embodiments, the data entry system may take the form of a remote personal computer or tablet device that wirelessly transmits entered patient indicators to the EMR database 1720 and/or the scoring system 1730. If desired, the EMR database 1720 and/or the scoring system 1730 may send information back to the remote computer system or mobile device to provide real-time feedback to the health care worker possessing the mobile device or operating the remote personal computer.

Figure 17B:
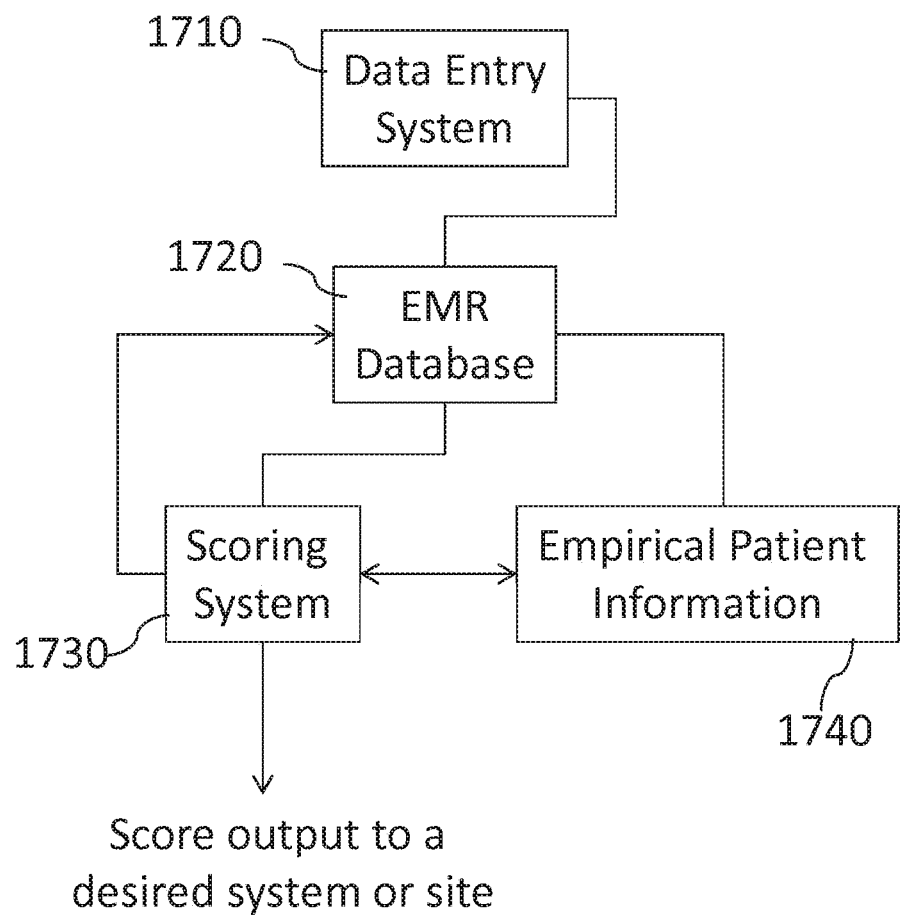
FIG. 17B is schematic of a system for scoring that can access an electronic medical record and empirical patient information, in accordance with certain examples.

In some embodiments and referring to FIG. 17B, the scoring system 1730 may be linked or coupled to empirical patient information 1740, which may take the form of a database that includes statistical numbers, e.g., averages and standard deviations, of various patient indicators. As a patient indicator value is received by the scoring system 1730, the system 1730 may compare the received value to a value in the empirical patient information (EPI) 1740. The comparison permits the scoring system 1730 to select the appropriate score for that particular patient indicator. In some examples, the empirical patient information can be updated in real-time as statistical entries into electronic medical records can be captured and stored in the empirical patient information system 1740. For example, the system 1740 may include de-identified patient information that is representative of various values extracted from patient electronic medical records. In some instances, the system 1740 may be a repository for combined patient statistics for a particular health system, e.g., the Carillion Clinic health system, such that patient values for all electronic medical records may be combined (de-identified if desired) and stored in the system 1740. In certain examples, the system 1740 may be configured to permit remote polling or comparison so that hospitals or care centers outside of the health system can access the EPI for purposes of calculating patient scores within a unit. In addition, external hospitals or care centers may poll the EPI system 1740 with their patient indicators to determine patient scores, composite scores and/or population scores.

It is a substantial attribute of the systems and methods described herein that scores can be calculated from the time of patient admission up to the time of patient discharge (or death) to provide improved indicators of staffing workload and patient health status. As noted herein, certain patient indicators may be staggered as patient discharge (or patient death) does not necessarily result in an immediate drop in staffing workload. In certain instances, the systems described herein are configured such that weighted composite scores for each of the plurality of patients from the time of patient admission to the time of patient discharge or patient death are calculated. As patients are discharged, scores can be updated based on current patient load. If desired, the population score for a particular set of patients can be weighted by an additional weighting factor. For example, population scores for intensive care units may be weighted by 5% or more such that adequate staffing levels are always present in those units. The weighted population scores may be compared in real-time to other population scores, as described herein, to assess whether staffing levels may need to be redistributed. Population scores for one or more units may be projected out to a desired period to determine if staffing levels at that period will be adequate for the particular projected population score. If desired, the trend line may be summed to provide a composite trend line that can be used to assess staffing levels. In certain instances, if the slope of the composite trend line exceeds a certain value (or decreases by a certain value), then staffing levels can be adjusted accordingly. In some examples, any one or more of the population scores can be compressed within a desired scale to simplify their review or individual composite scores can be compressed and then summed.

In some embodiments, at least two, three, four or five of the patient indicators shown in Table I in FIGS. 1-4D can be used to determine a composite score. In other embodiments, at least five, ten, fifteen, twenty, twenty-five, thirty, thirty-five, forty, forty-five, fifty or more patient indicators are used to determine a composite score.

In certain embodiments, the compressed scores may be implemented and used throughout the system to simplify the overall review of various scores. By compressing scores, fewer scores need to be considered for determining staffing levels. In some embodiments, the system is configured to determine a composite patient indicator score for each of a plurality of patients by scoring patient indicators using scores derived from empirical patient data. The system may also compress each of the determined, composite patient indicator scores between a selected range. The compressed scores can be summed to provide a compressed population score. Staffing levels may then be based on the compressed population score.

In certain examples, the composite patient indicator scores are determined by using a weighting factor scale range for each of the patient indicators, in which the weighting factor scale range is different for at least two of the patient indicators. In other embodiments, patient indicators representative of a higher mortality risk have a greater range of values, e.g., five potential values, than a patient indicator representative of a lower mortality risk, e.g., two potential values. As noted herein, patient indicators may be extracted from electronic medical records to determine compressed population scores. If desired, compressed population scores can be weighted according to the particular unit. In some instances, a compressed population score for each unit of a hospital may be determined and compared to compressed population scores of other units. In certain embodiments, the compressed population scores can be used to predict future compressed population scores and adjust staffing needs accordingly. In some embodiments, trend lines may be generated and summed together to provide a composite trend line. The composite trend lines may be used to identify if staffing levels should be adjusted in the future. As noted herein, the scores assigned to a particular patient indicator may be weighted based on empirical patient data with different patient indicators having different score ranges. In some embodiments, at least two, three, four or five of the patient indicators shown in Table I in FIGS. 1-4D can be used to determine a compressed composite score or a compressed population score or both. In other embodiments, at least five, ten, fifteen, twenty, twenty-five, thirty, thirty-five, forty, forty-five, fifty or more patient indicators are used to determine a compressed composite score or a compressed population score or both.

In certain examples, the indicators described herein can be used to provide subscores which may be a combination of scores from two, three, four, five or more indicators. In some embodiments, the subscores can be compressed as described herein. In other instances, a composite score considering all indicators and a composite subscore considering selected indicators can each be calculated and used to assess patient outcomes. For example, while a patient's overall score may not be within a range that is considered dangerous, certain subscores, e.g., those including physiological parameters or lab tests, may be within a dangerous range to merit additional staffing intervention. By calculating by a composite score and a composite subscore, either or both of which can be compressed, additional information about a patient's health status and the suitable staffing levels for caring for the patient can be assessed. In certain embodiments, certain indicators can be correlated with each other to predict patient outcomes. For example, it may be desirable to group certain indicators to provide a composite subscore if those indicators are associated with higher mortality or reduced outcomes for a particular patient or group of patients. If desired, the subscores can be categorized according to a three level ranking, e.g., red, yellow, green, so subscores can be visually monitored. In particular, the subscores may be visualized in any manner similar to the manner used to visualize or display composite scores, compressed scores or other scores described herein.

In certain embodiments, the systems and methods described herein can be used in an ambulatory care setting, which may include centers or sites within a hospital, stand-alone care centers or a patient's residence. The particular patient indicators in an ambulatory care setting may differ from those used in a hospital setting. For example and referring to FIG. 18, Table 6 lists certain outpatient indicators and their associated scores that can be used in place of, or in addition to, those patient indicators shown in Table 1. One outpatient indicator which is shown is a score for revisiting within a defined period. For example, if the patient returns to the ambulatory care setting within 2 days, then a score of 3 is assigned. At least some of the patient indicators in Table 6 can be used to determine a composite outpatient indicator score for each of a plurality of outpatients by scoring outpatient indicators using scores derived from empirical outpatient data. For example, empirical data representative of a particular patient indicator can be used to assign a particular score value for that patient indicator. The individual scores for a particular patient can be summed to provide a composite outpatient score. All composite outpatient scores may be summed to provide an outpatient population score, which can be used to assign a staffing level to the ambulatory care setting. For example, the outpatient population score can be correlated with values in a lookup table to assign the proper level of staffing. Referring to Table 7 of FIG. 19, an outpatient population score of 45 would be indicative of 2 licensed workers and 1 unlicensed worker being a desirable staffing level. An outpatient population score of 127 would be indicative of 4 licensed workers and 3 unlicensed workers being desirable staffing levels. As most ambulatory care settings have limited examination rooms, if a population score exceeds a certain level it may not be desirable to increase staffing further as increased staffing may not result in faster patient examination where all examination rooms are already occupied.

In certain embodiments, the systems described herein may be configured to determine composite outpatient indicator score using a weighting factor scale range for each of the outpatient indicators, in which the weighting factor scale range is different for at least two of the outpatient indicators. As shown in Table 6, the scale for the particular outpatient indicators is not the same. Certain outpatient indicators can be weighted more than others. For example, an outpatient indicator representative of a higher risk has a greater range of values than an outpatient indicator representative of a lower risk. As described in reference to the patient indicators, outpatient indicators can be extracted from an electronic medical record automatically. If desired, a composite outpatient indicator score for each of the plurality of outpatients can be determined by the system from the time of patient triage to the time of patient discharge. To facilitate early scoring, it may be desirable for a patient to fill out an admission or visitation form electronically so patient responses may be used immediately in calculating a composite outpatient score. In some embodiments, the outpatient population score can be weighted. For example, where many different ambulatory care units are present in a hospital, e.g., family practice, internal medicine, dermatology, pediatrics, gynecology, psychiatry, etc., it may be desirable to weight the population scores of a particular unit more than other units. Staffing can be assigned (or redistributed) among the various ambulatory care units based on comparison of the weighted outpatient population scores. In some embodiments, the system may determine an outpatient population score for each ambulatory care unit of a hospital. In certain examples, the outpatient population scores for each unit may be graphically displayed, e.g., color coded or displayed as actual values, so an administration may readily determine staffing needs for the various units. In some embodiments, the outpatient population scores can be used to predict future staffing needs. For example, scores can be used to provide trend lines that may be used to assess staffing needs at a future time. Individual composite outpatient score trend lines can be summed, if desired, to provide a representation of the entire population. In some examples, the outpatient population scores can be compressed, e.g., compressed over a scale of 1 to 10. In some embodiments, at least two, three, four, five, six, seven, eight, nine or all of the outpatient indicators shown in Table 6 may be used in determining a composite outpatient score. If desired one or more patient indicators from Table 1 can also be used in combination with the outpatient indicators to provide a composite outpatient score. For example, at least five, ten, fifteen, twenty, twenty-five, thirty, thirty-five, forty, forty-five, fifty or more patient indicators can be used along with one or more outpatient indicators to determine a composite score or a population score or both.

In certain examples, the systems and methods described herein can be used to determine staffing levels in a nursing home or rehabilitation center. For example, resident indicator values can be used to determine a composite resident indicator score for each of a plurality of residents (or rehabilitants) in a nursing home or rehabilitation center. In some instances, the composite resident indicator scores can be derived from empirical resident data. In certain embodiments, the system may sum the composite indicator scores of the plurality of residents to provide a resident population score (or a rehabilitant population score). Staff levels may then be assigned or assessed using the summed resident population scores. Referring to Table 8 in FIG. 20, illustrative resident indicators and corresponding scores are shown. For example, resident with late stage dementia receive a score of 3 for that indicator, whereas residents with no dementia receive a score of 0 for that indicator. As described in reference to the patient and outpatient indicators, resident indicators can be extracted from an electronic medical record automatically. If desired, a composite resident indicator score for each of the plurality of residents can be determined by the system from the time of resident admission to the time of resident discharge (or death). To facilitate early scoring, it may be desirable for a resident to fill out an admission or visitation form electronically so resident responses may be used immediately in calculating a composite resident score. In certain embodiments, a resident population score can be calculated by summing the individual composite resident scores. In some embodiments, the resident population score can be weighted. For example, where many different resident care units are present in a nursing home, e.g., dementia unit, assisted care unit, etc., it may be desirable to weight the population scores of a particular unit more than other units. Staffing can be assigned (or redistributed) among the various resident units based on comparison of the weighted resident population scores. In some embodiments, the system may determine a resident population score for unit of a nursmg home. In certain examples, the resident population scores for each unit may be graphically displayed, e.g., color coded or displayed as actual values, so an administration may readily determine staffing needs for the various units. In some embodiments, the resident scores can be used to predict future staffing needs. For example, scores can be used to provide trend lines that may be used to assess staffing needs at a future time. Individual composite resident score trend lines can be summed, if desired, to provide a representation of the entire population of residents. In some examples, the resident population scores can be compressed, e.g., compressed over a scale of 1 to 10. In some embodiments, at least two, three, four, five, six, seven, eight, nine or all of the resident indicators shown in Table 8 may be used in determining a composite resident score. If desired one or more patient indicators from Table 1 can also be used in combination with the resident indicators to provide a composite resident score. For example, at least five, ten, fifteen, twenty, twenty-five, thirty, thirty-five, forty, forty-five, fifty or more resident indicators can be used along with one or more resident indicators to determine a composite score or a population score or both. A correlation table similar to that shown in Table 7 of FIG. 19 can be used to determine suitable staffing levels for the various resident units.

In other examples, the systems and methods described herein can be used to assess staffing levels at various military field hospitals. For example, military field hospitals may be erected at various remote military bases or at remote engagement sites. The particular composite patient indicator score at each of these facilities can be used to assess which facilities may require higher staffing levels. In some instances, the composite soldier scores can be derived from empirical soldier data. In certain embodiments, the system may sum the composite solider scores of the plurality of soldiers to provide a soldier population score. Staff levels may then be assigned or assessed using the summed soldier population scores. Referring to Table 9 in FIG. 21, illustrative soldier indicators and corresponding scores are shown. For example, soldiers with second degree burns receive a score of 2 for that indicator, whereas soldiers with no burns receive a score of 0 for that indicator. As described in reference to the patient and outpatient indicators, soldier indicators can be extracted from an electronic medical record automatically. Alternatively, soldier indicators can be extracted from a mobile device where a medic may enter a soldier's condition. The remote device can transmit the soldier indicators to a command center or central medical center for use in determining a composite soldier score. If desired, a composite soldier indicator score for each of the plurality of soldiers in a military field hospital (and/or in route to a military field hospital) can be determined by the system from the time the wounded soldier is triaged to the time of discharge (or death). In certain embodiments, a soldier population score can be calculated by summing the individual composite soldier scores. In some embodiments, the soldier population score can be weighted. For example, where many different military field hospital units are present in a theater, it may be desirable to weight the population scores of a particular unit, e.g., one closer to active battle or engagements, more than other field hospitals. Staffing can be assigned (or redistributed) among the various field hospital units based on comparison of the weighted soldier population scores. In some embodiments, the system may determine a soldier population score for military field hospital within a desired area or country. In certain examples, the soldier population scores for each field hospital unit may be graphically displayed, e.g., color coded or displayed as actual values, so an administrator may readily determine staffing needs for the various field units. In some embodiments, the soldier scores can be used to predict future staffing needs. For example, scores can be used to provide trend lines that may be used to assess staffing needs at a future time. Individual composite soldier score trend lines can be summed, if desired, to provide a representation of the entire population of soldiers. In some examples, the soldier population scores can be compressed, e.g., compressed over a scale of 1 to 10. In some embodiments, at least two, three, four, five, six, seven, eight, nine or all of the soldier indicators shown in Table 9 may be used in determining a composite soldier score. If desired one or more patient indicators from Table 1 can also be used in combination with one or more soldier indicators to provide a composite soldier indicator score. For example, at least five, ten, fifteen, twenty, twenty-five, thirty, thirty-five, forty, forty-five, fifty or more resident indicators can be used along with one or more soldier indicators to determine a composite score or a population score or both. A correlation table similar to that shown in Table 7 of FIG. 19 can be used to determine suitable staffing levels for the various field hospital units.

Figure 22:
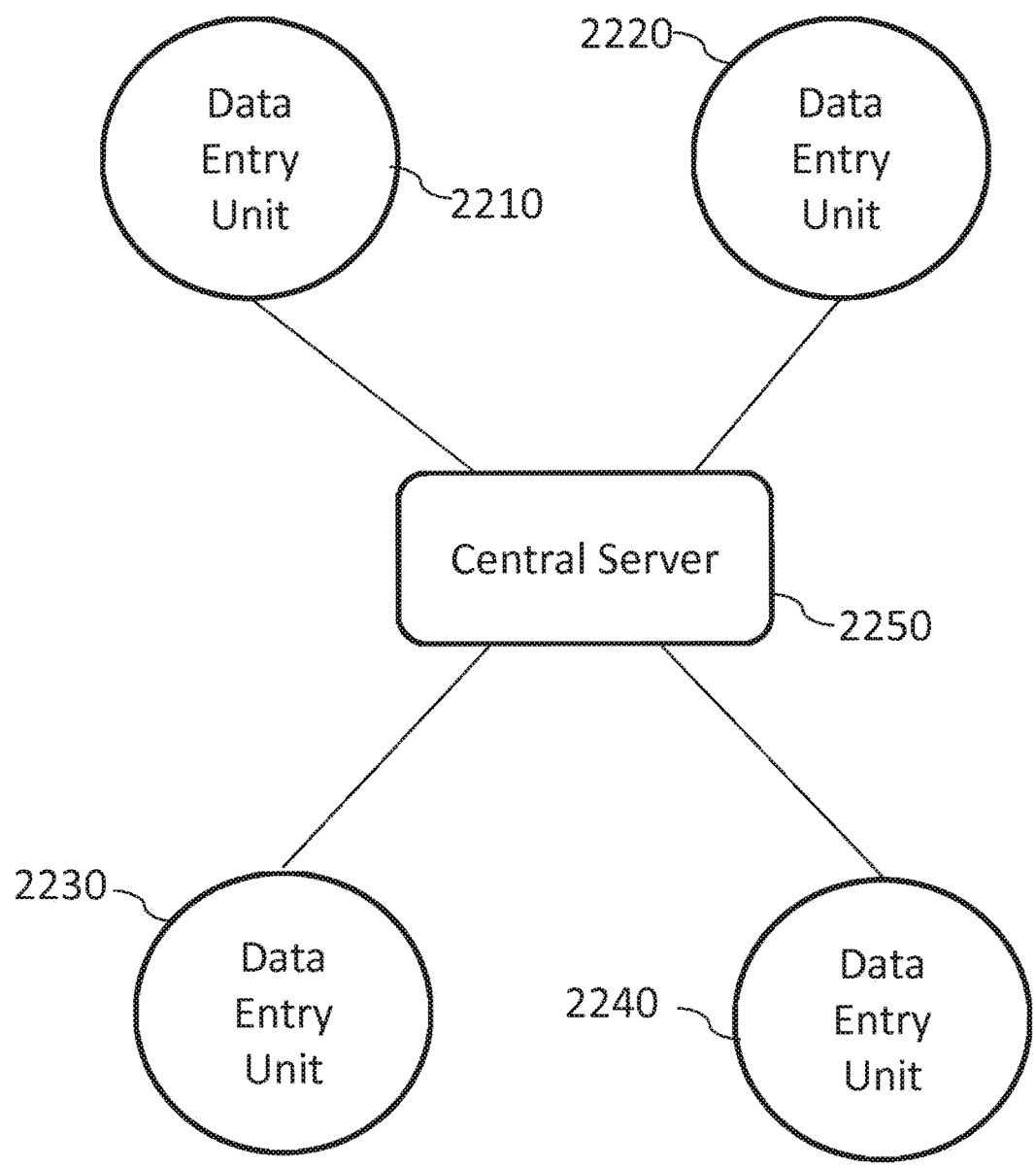
FIG. 22 is an illustration of a system that can received patient indicators from a plurality of different data entry systems, in accordance with certain examples.
Figure 23:
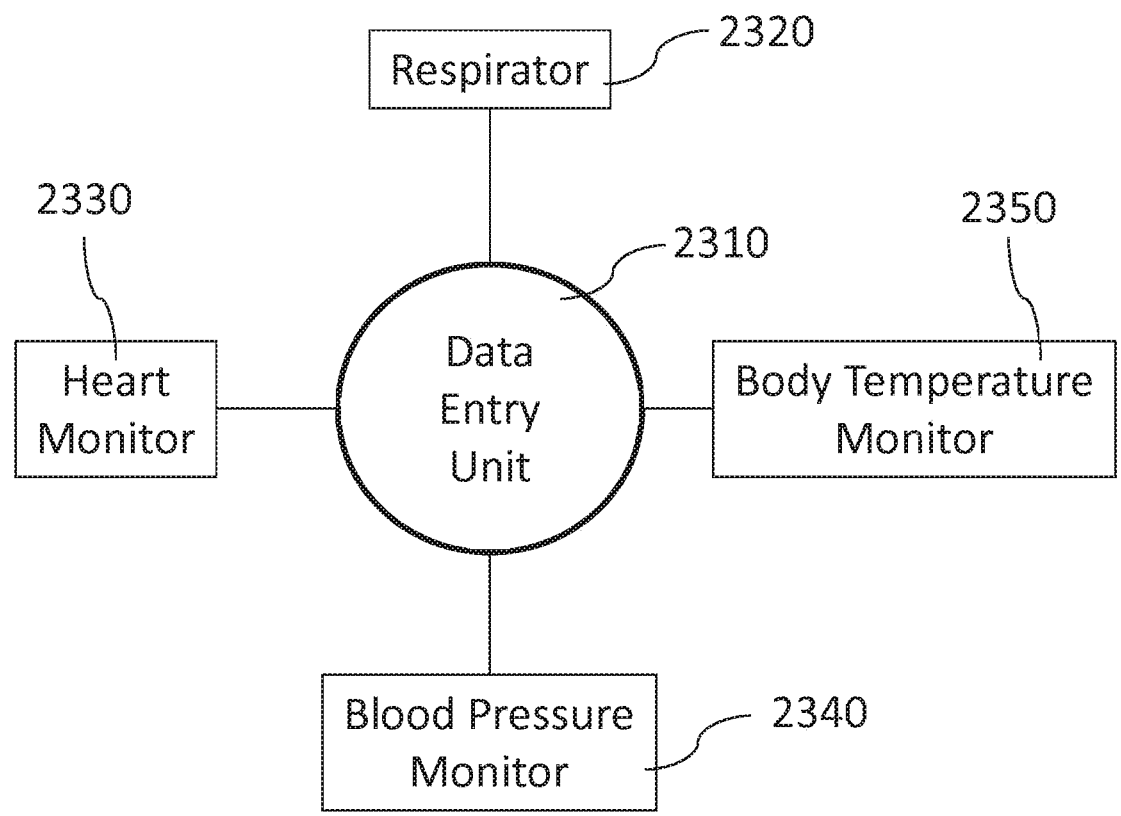
FIG. 23 is an illustration of a system where different supporting devices are coupled to a data entry system, in accordance with certain examples.

In the various systems described herein, there may exist a plurality of separate data entry devices that communicate with a central system that can receive the indicators, calculate scores using empirical patient information, store the scores or otherwise use the scores for a desired purpose. Referring to FIG. 22, a system 2200 is shown comprising a plurality of data entry units 2210-2240 each of which is coupled to a central server 2250. The data entry units 2210-2240 may be the same or may be different. In some embodiments, the data entry units 2210-2240 can be wirelessly coupled to the server 2250 or coupled through one or more wires or cables. In certain instances, one or more of the data entry units 2210-2240 may take the form of a personal computer, a mobile device, e.g., a phone or tablet device, or other electronic devices which can permit data entry and subsequent transfer to the server 2250. In some configurations, other electronic devices present in a patient's room may also be coupled to the central server 2250, the data entry unit or both. For example and referring to FIG. 23, a data entry unit 2310 is shown as being coupled to a respirator 2320, a heart monitor 2330, a blood pressure monitor 2340, and a body temperature monitor 2350. Patient indicators may be sent from one or more of the devices 2320-2350 to the data entry unit 2310 through suitable circuitry, e.g., through signal processors or the like. The data entry system 2310 can transmit the patient indicators received from the devices 2320-2350 to a server or other system that can use the transmitted patient indicators to determine a score for the patient indicators and/or calculate a composite score for the patient. In some embodiments, the data entry unit 2310 may transmit the received patient indicators 2320-2350 in real time or may transmit the patient indicators at periodic intervals, e.g., every minute, every five minutes, every ten minutes, every fifteen minutes, every twenty minutes, every thirty minutes, every hour, every two hours, every three hours, every four hours or at other desired intervals. Similar data entry units can be present in each patient room to provide patient indicators from each room that may be used to determine a population score for all patients in a particular unit. The population scores may be used as described herein to determine a level of staffing for the particular unit or care setting. If desired, there may be a central server for an entire care facility or each unit of the care facility can include a respective server where scores are determined. In some embodiments, the server can provide the determined scores back to the data entry unit or to another desired device for display or review. In addition, the server may color-code the scores (or code the scores in some other manner) prior to transmission to a desired device.

In certain embodiments, the systems described herein, and their methods of using them can be implemented using a computer or other device that includes a processor. The computer system typically includes at least one processor electrically coupled to one or more memory units to receive input data from staff and/or retrieve lookup tables for assigning scores. The computer system may be, for example, a general-purpose computer such as those based on Unix, Intel PENTIUM-type processor, Motorola PowerPC, Sun UltraSPARC, Hewlett-Packard PA-RISC processors, or any other type of processor. One or more of any type computer system may be used according to various embodiments of the technology. Further, the system may be located on a single computer or may be distributed among a plurality of computers attached by a communications network. In particular, the system may comprises a plurality of individual computers, e.g., personal computers or mobile devices such as tablets, that can permit entry of individual patient indicators and transmit those patient indicators to a central server to permit scoring of the transferred patient indicators. A general-purpose computer system may be configured, for example, to perform any of the described functions including but not limited to: patient indicator entry, indicator scoring, score weighting, trigger alerts or the like. It should be appreciated that the system may perform other functions, including network communication, and the technology is not limited to having any particular function or set of functions.

Various aspects of the systems and methods may be implemented as specialized software executing in a general-purpose computer system. For example, an electronic medical record configured to receive input data where a nurse or other staff selects suitable patient indicators from a menu or on-screen many be implemented. The computer system may include a processor connected to one or more memory devices, such as a disk drive, memory, or other device for storing data. Memory is typically used for storing programs and data during operation of the computer system. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically is electrically coupled to a power source and/or one or more supporting devices, e.g., respirator, heart monitor, etc., such that electrical signals may be provided to and from the computer and the supporting devices to provide automated patient indicators. The computer system may also include one or more input devices, for example, a keyboard, mouse, trackball, microphone, touch screen, manual switch (e.g., override switch) and one or more output devices, for example, a printing device, display screen, speaker. In addition, the computer system may contain one or more interfaces that connect the computer system to a communication network (in addition or as an alternative to the interconnection device). The computer system may also include suitable circuitry to convert signals received from supporting devices to a desired form to permit scoring of the signals representative of a patient indicator. Such circuitry can be present on a printed circuit board or may be present on a separate board or device that is electrically coupled to the printed circuit board through a suitable interface, e.g., a serial ATA interface, ISA interface, PCI interface or the like.

In certain embodiments, the storage system of the computer typically includes a computer readable and writeable nonvolatile recording medium in which signals are stored that define a program to be executed by the processor or information stored on or in the medium to be processed by the program. For example, polling times, current patient indicators or other features may be stored on the medium. The medium may, for example, be a disk, solid state drive or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. For example, the processor may assign the weighted scores for each patient indicator and store them in the medium. If desired, the weighted scores can be summed, and the summed score can be stored in the medium. A variety of mechanisms are known for managing data movement between the medium and the integrated circuit memory element and the technology is not limited thereto. The technology is also not limited to a particular memory system or storage system.

In certain embodiments, the computer system may also include specially-programmed, special-purpose hardware, for example, an application-specific integrated circuit (ASIC) or a field programmable gate array (FPGA). Aspects of the technology may be implemented in software, hardware or firmware, or any combination thereof. Further, such methods, acts, systems, system elements and components thereof may be implemented as part of the computer system described above or as an independent component. Although a computer system is described by way of example as one type of computer system upon which various aspects of the technology may be practiced, it should be appreciated that aspects are not limited to being implemented on the described computer system. Various aspects may be practiced on one or more computers having a different architecture or components. The computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP, Windows Vista, Windows 7 or Windows 8 operating systems available from the Microsoft Corporation, MAC OS X, e.g., Snow Leopard, Lion, Mountain Lion or other versions available from Apple, the Solaris operating system available from Sun Microsystems, or UNIX or Linux operating systems available from various sources. Many other operating systems may be used, and in certain embodiments a simple set of commands or instructions may function as the operating system.

In certain examples, the processor and operating system may together define a computer platform for which application programs in high-level programming languages may be written. It should be understood that the technology is not limited to a particular computer system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate computer systems could also be used. In certain examples, the hardware or software is configured to implement cognitive architecture, neural networks or other suitable implementations. If desired, one or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In some instances, various embodiments may be programmed using an object-oriented programming language, such as SmallTalk, Basic, Java, C++, Ada, or C # (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof.

In certain embodiments, the system may take the form of a mobile device, e.g., a phone or a tablet, that is configured to permit entry of patient indicators and transmit the patient indicators to a central system. The central system may score the patient indicators as described herein, and can transmit the weighted scores back to the patient's room for display on a computer within the patient's room or may track the weighted scores over time for trending purposes. In some instances, the computer within the patient's room may periodically transmit updated patient indicators, e.g., to the mobile device, such that nursing staff or other staff have real-time feedback of a patient's status.

Figure 24:
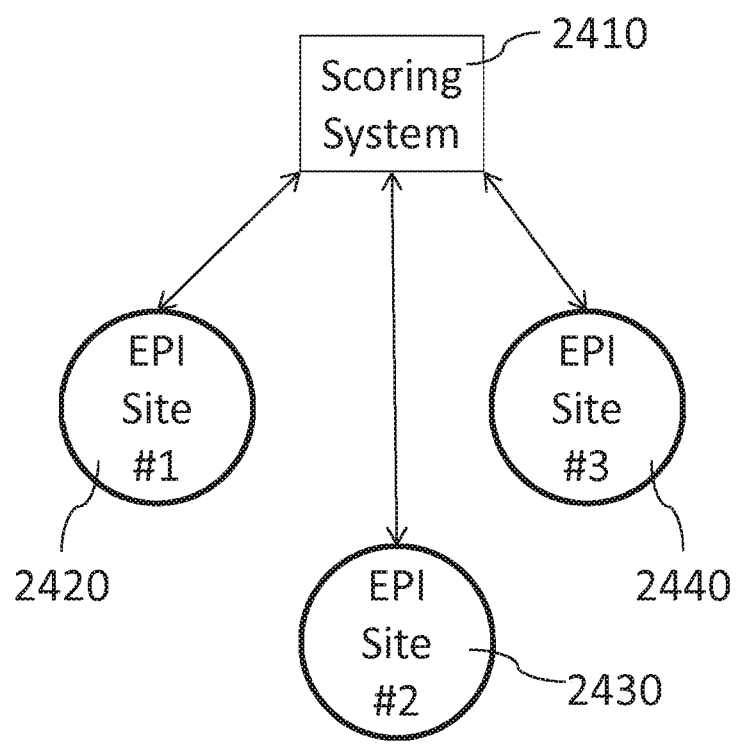
FIG. 24 is an illustration of a system that can access multiple different systems including empirical patient information or data, in accordance with certain examples.

In some examples, the systems described herein may access a plurality of different empirical patient information (EPI) for scoring. For example and referring to FIG. 24, a scoring system 2410 is shown that can access a plurality of different EPI sites 2420, 2430 and 2440. In some instances, the EPI systems 2420, 2430 and 2440 may be present in the same hospital, whereas in other instances one of more of the EPI systems 2420, 2430 and 2440 may be located remote from each other. For example, the different EPI systems 2420, 2430 and 2440 can be located in different hospitals but may be accessible by a scoring system in any one particular hospital or other site. If desired, the scoring system 2410 can access patient information in the EPI systems 2420, 2430 and 2440 to compare a particular patient indicator to an average value calculated from the information in the EPI systems 2420, 2430 and 2440. The exact number of EPI systems used in determining a patient score can vary from about two to about five or more. In some embodiments, the scoring system 2410 can be configured to calculate a first score for a particular patient indicator using only one EPI system, and calculate a second score using EPI from two EPI systems. If the scores differ by more than a threshold value, e.g., 5%, then a third EPI system may be accessed and used to calculate a third score. The closest two scores can be used to provide an average score that may be used in determining the composite patient score. By assigning a score after comparison to multiple different EPI systems, the score for a particular patient indicator can be more accurate. In some instances, the EPI systems 2420, 2430 and 2440 can be updated in real time as new patient information is being collected through electronic medical records. The ability of the scoring system to access constantly updating EPI systems increased the overall accuracy and precision of the scoring systems and methods described herein.

Figure 25:
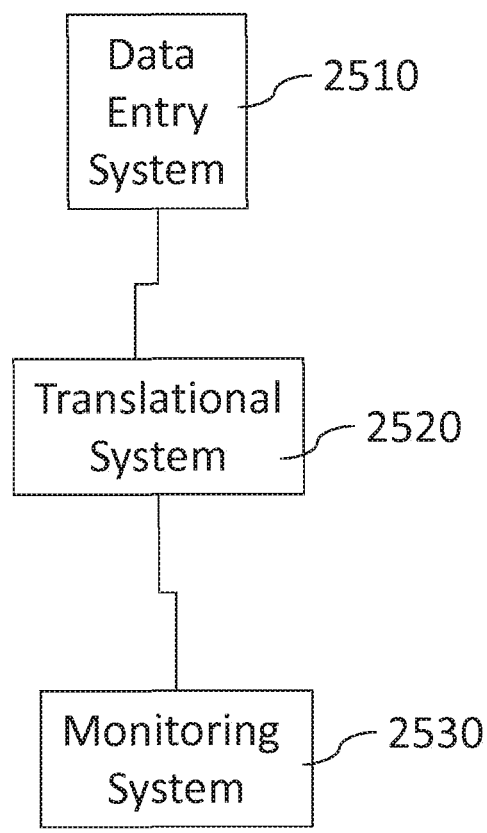
FIG. 25 is an illustration of a system comprising a data entry system, a translational system and a monitoring system, in accordance with certain examples.

In certain examples, each particular component of the scoring systems described herein may be present as a separate and distinct system. Referring to FIG. 25, a system 2500 is shown that includes a data entry system 2510, a translational system 2520, and monitoring system 2530. Each of the systems 2510, 2520 and 2530 typically includes a processor and one or more memory units and or storage units. The data entry system 2510 is configured to receive input from staff regarding patient health, vitals, and other patient statistics. The translational system 2520 receives information from the data entry system and converts that information into a score. In some embodiments, the translational system is configured to search for keywords in information from the data entry system 2510 and use those keywords to identify patient indicators. The patient indicators may then be converted to a score as described herein, e.g., using a lookup table. The translation system 2520 may then sum the scores for all patient indicators to provide a composite patient indicator score and/or, if desired, may sum all composite patient indicator scores to provide a population score. As noted in reference to FIG. 24, the translational system 2520 may access one or more EPI systems to compare the patient indicators to empirical averages and ranges and determine a score based on that comparison. The score provided by the translation system 2520 can be provided to the monitoring system 2530, which may output the actual score, color code the score or otherwise monitor one or more scores and, for example, send an alert to an administrator or other personnel if the scores change by more than a threshold amount over a selected period. While the systems 2510, 2520 and 2530 are shown as being coupled in FIG. 25, the systems 2510, 2520 and 2530 may be wirelessly coupled, located remote from each other or otherwise not directly linked to each other through a hard-wire connection.

In certain embodiments, the systems and methods described herein can be used to assess likelihood of readmission. For example, composite patient indicator scores prior to discharge can be used to assess whether or not the patient will likely be readmitted within a selected period, e.g., 30 days. In some embodiments, the EPI may include a lookup table correlating composite or compressed patient indicator scores with readmission rates at selected times prior to discharge, e.g., 2 hours prior to discharge, 4 hours prior to discharge, etc. In other embodiments, the trend line of patients prior to discharge may be used and compared with trends in an EPI system to assess likelihood of readmission. In other embodiments the mean time of the patients stay may be used with or without a composite of two or more other indicators to identify patients anticipated to be readmitted or use additional resources between hospitalizations or determine disposition resources required. Where it is determined that patient is at risk for readmission, additional therapy intervention or follow up therapy may be scheduled to reduce the likelihood of readmission. The systems for assessing readmission likelihood may include a scoring system and optionally one or more EPI systems, if desired.

In certain embodiments, the systems and methods described herein can be used to assess the financial impact and risk for a particular patient, group, population, or unit. For example, the level of staffing predicted can be compared to the actual level of staffing and overall patient outcomes to determine if a suitable level of staffing was present over a selected period. If the predicted staffing levels are less than the actual staffing levels and patient outcome was positive, then a reduction of staffing levels may be in order. Similarly, if patient outcomes where negative and staffing levels were less than recommended, then staffing levels can be subsequently increased. In addition to the overall score, it may be desirable to consider the actual time staff spent in patient rooms treating patients. Such time can be recorded automatically through the use of RFID tags, interne tracking devices or other devices that can track when staff enter and exit patient rooms, homes and other settings or otherwise are interacting with a patient. In situations where little time is spent in patient rooms, it may be desirable to adjust staffing levels to include more personnel not typically associated with direct patient treatment.

In certain examples, the various scores described herein may be used in conjunction with, or instead of, relative value units (RVUs) commonly used to determine physician payments and/or salaries. RVUs are often tied to Medicare payments. For example, for a particular service provided, a payment formula containing three RVUs, one for physician work, one for practice expense, and one for malpractice expense can be used. The three RVUs for a given service are each multiplied by a unique geographic practice cost index. The sum of the three geographically weighted RVU values is then multiplied by the Medicare conversion factor to obtain a final price. In some examples, the scores described herein can be used as weighting factors for the RVUs or may be used in place of the RVUs as a better measure of the time needed to provide effective patient care. If desired, to better assess equivalent values of RVUs based on the scoring described herein, the scores may be broken into more categories, e.g., 2, 1.5, 1, 0.5 0.25, etc., to provide a broader range of values for each particular indicator.

In certain configurations, the indicators and scores described herein can be used to assess the mortality risk of a particular patient or a patient population, e.g., a set of patients in an intensive care unit, nursing home, ambulatory care setting or any one of the other care settings described herein. While a plurality or all of the indicators described herein can be used to predict mortality, it may be desirable in certain instances to use a subset of indicators which have been empirically correlated to be better predictors of mortality than other indicators. The mortality risk may be color coded or scaled to a score, e.g., 1, 2 or 3 with 1 being the lowest risk and 3 being the highest risk, to provide rapid visual feedback to staff. A trend or trendline of the mortality risks can be used to predict a future mortality risk, which can lead to quicker intervention and/or increased medical care.

In certain embodiments, the scores described herein may be used with one or more mortality indicators to asses a mortality risk for a patient or an entire patient population. For example, a composite patient indicator score can be determined for each of a plurality of patients at a first period by scoring patient indicators using scores derived from empirical patient, device, or other source system data. A mortality risk value for each patient of the population can be generated from a plurality of mortality indicators and the composite patient indicator score of the patient. If desired, the system may compare the mortality risk value for each patient to a threshold value to provide a mortality risk for each patient of the patient population. In some instances, the mortality indicators used may be two, three, four, five, six, seven, eight, nine, ten or more of the following mortality indicators: Maximum Hour of Stay, Age of patient, Mean Acuity total score, Mean Systolic Blood Pressure, Mean Glasgow coma score or Neurological Status, Mean Urine Output, Median Acuity total score, Median Systolic Blood Pressure, Median Glasgow coma score or Neurological Status, Median Urine Output, Min Acuity total score, Min Systolic Blood Pressure, minimum Glasgow coma score or Neurological Status, Minimum Urine Output, maximum Acuity total score, maximum Systolic Blood Pressure, maximum Glasgow coma score or Neurological Status, maximum urine Output, range Acuity total score, range Systolic Blood Pressure, Range Glascow coma score or Neurological Status, Range Urine Output, Gender Female and/or Gender Male.

In some configurations, a staffing level may be assigned based on the patient mortality risk values. In other instances, the mortality risk value can be generated using a neural network model and the mortality risk values and composite patient indicator scores. If desired, the patient indicators and the mortality indicators can be extracted from an electronic medical record, device or other electronic source. In some instances, the determined mortality risk values can be graphically displayed for each patient on the unit. For example, a color-coded bar chart may appear for each patient showing the mortality risk value over time, e.g., green for low risk, yellow for medium risk and red for high risk. Such bar graph coding provides rapid visual feedback to staff. In certain examples, the future or mortality risk value trend can be extrapolated to assess whether staffing needs should be changed at a later time, e.g., 1 hour, 2 hours, 3 hours, etc. Mortality risk values may be determined at periodic intervals to assess staffing levels, e.g., staffing levels on the unit can be increased if the average patient population mortality risk value increases by a selected amount over the period.

In instances where the mortality risk for an individual patient is determined, a patient score can be used in combination with a plurality of mortality indicators to generate a mortality risk value for that patient. If desired, the generated mortality risk value can be compared to a threshold value to provide a mortality risk for the patient. Staffing level for the particular patient may be assigned based on the mortality risk determined for that patient. This analysis permits risk assessment on a patient by patient basis. In some instances, the mortality risk value is generated using a neural network model and the mortality risk values and composite patient indicator scores. The patient indicators and the mortality indicators can be extracted from an electronic medical record, device or other electronic source. In some configurations, the mortality risk for the patient can be graphically displayed over a period, e.g., the risk can be color-coded using at least a three level color coding scheme. In certain instances, the method may comprise predicting a future mortality risk for the patient by determining a trend for the mortality risk over the period. In some examples, the mortality risk value is determined at periodic intervals from the time of patient admission to the time of patient discharge. In certain embodiments, the mortality risk for the patient is determined over a period to assess staffing levels assigned to the patient. In some instances, staffing levels are increased if the mortality risk of the patient increases by a threshold amount over the period.

In other configurations, mortality risk of a resident population in a nursing home can be determined. For example, a composite resident indicator score can be determined for each of a plurality of nursing home residents on a nursing home unit by scoring resident indicators using scores derived from empirical resident data. A mortality risk value can be generated for each resident of the nursing home unit from a plurality of mortality indicators and the composite patient indicator score of the patient. In some embodiments, the mortality risk value can be compared for each resident of the nursing home unit to a threshold value to provide a mortality risk for each resident of the nursing home unit. In some configurations, a staffing level can be assigned to the unit based on the resident mortality risk values. In certain instances, the mortality risk value is generated using a neural network model and the mortality risk values and composite resident indicator scores. In some embodiments, the resident indicators and the mortality indicators can be extracted from an electronic medical record, device or other electronic source. If desired, the determined mortality risk values can be graphically displayed for each resident on the unit, e.g., may be color coded using at least a three level color coding scheme. One or more trends or trendlines can be used to assess a future mortality risk by determining a trend for the mortality risk values. The mortality risk can be determined at periodic intervals. In some instances, an average resident mortality risk is determined over a period to assess staffing levels. In certain situations, staffing levels on the unit are increased if the average resident mortality risk increases by a selected amount over the period.

In other embodiments, a method of assessing mortality risk for a particular resident of a nursing home may be performed. In some configurations, a composite resident indicator score for the resident is determined at a first period by scoring resident indicators using scores derived from empirical patient, device, or other source system data. The composite resident indicator scores of the resident can be summed to provide a resident score. A mortality risk value for the resident can be determined from a plurality of mortality indicators and the resident score. If desired, the generated mortality risk value can be compared to a threshold value to provide a mortality risk for the resident. In some instances, a staffing level may be assigned to the particular resident based on the mortality risk. In some configurations, the mortality risk value is generated using a neural network model and the mortality risk values and composite resident indicator scores. In other configurations, the resident indicators and the mortality indicators can be extracted from an electronic medical record, device or other electronic source. In some embodiments, the mortality risk for the resident can be graphically displaced over a period, e.g., color-coded using at least a three level color coding scheme. A trend or trendline can be used to predict the future mortality risk for the resident. In some instances, the mortality risk value is determined at periodic intervals, e.g., is determined over a period to assess staffing levels assigned to the patient. If desired, staffing levels can be increased if the mortality risk of the resident increases by a threshold amount over the period.

In certain embodiments, a mortality risk of a patient population in a military field hospital can be assessed. In some embodiments, a composite soldier indicator score for each of a plurality of soldiers at a military field hospital is determined by scoring soldier indicators using scores derived from empirical soldier data. In certain embodiments, a mortality risk value for each soldier of the military hospital is generated from a plurality of mortality indicators and the composite soldier indicator score of the patient. The generated mortality risk value for each soldier can be compared to a threshold value to provide a mortality risk for each soldier of the military field hospital. In some instances, a staffing level can be assigned to the military field hospital based on the soldier mortality risk values. In other configurations, the mortality risk value is generated using a neural network model and the mortality risk values and composite soldier indicator scores. In some embodiments, the soldier indicators and the mortality indicators can be extracted from an electronic medical record, device or other electronic source. In certain instances, each of the determined mortality risk values for each soldier of the military field hospital can be graphically displayed, e.g., color-coded using at least a three level color coding scheme or assigned a 1, 2 or 3 score as noted herein. A trend or trendline may be used to assess or predict a future mortality risk by determining a trend for the mortality risk values. If desired, the mortality risk is determined at periodic intervals or over a period to assess staffing levels. In some instances, staffing levels of the military field hospital are increased if the average soldier mortality risk increases by a selected amount over the period.

In certain embodiments, a mortality risk for a particular soldier in a military field hospital can be assessed. For example, a composite soldier indicator score for the soldier at a first period can be determined by scoring soldier indicators using scores derived from empirical patient, device, or other source system data. The composite soldier indicator scores of the soldier can be summed to provide a soldier score. A mortality risk value for the soldier can be generated from a plurality of mortality indicators and the soldier score. If desired, the generated mortality risk value can be compared to a threshold value to provide a mortality risk for the soldier. In some examples, a staffing level can be assigned to the particular soldier based on the mortality risk. In some instances, the mortality risk value is generated using a neural network model and the mortality risk values and composite soldier indicator scores. In other configurations, the soldier indicators and the mortality indicators can be extracted from an electronic medical record, device or other electronic source. If desired, the mortality risk for the soldier over a period can be graphically displayed, e.g., by color-coding the risk using at least a three level color coding scheme. In some instances, a future mortality risk for the soldier can be predicted by determining a trend for the mortality risk over the period. In other instances, the mortality risk value is determined at periodic intervals or is determined over a period to assess staffing levels assigned to the soldier. In some examples, staffing levels are increased if the mortality risk of the soldier increases by a threshold amount over the period.

In certain embodiments, the scores and indicators described herein may be used in combination with mortality indicators to asses a mortality risk for a patient, resident, soldier or other person in a care setting. For example, patient indicators (or resident or soldier indicators) from a patient (or resident or soldier) can be compared to a scoring table comprising unequally weighted scores based on empirical patient data. A score can be assigned from the scoring table to each of the patient indicators. The assigned scores can be summed to provide a summed patient indicator score for the patient. The summed patient indicator score and a plurality of mortality indicators can be used to provide a mortality risk for the patient.

In other instances, patient indicators from each of a plurality of patients can be compared to a scoring table comprising unequally weighted scores based on empirical patient data. A score can be assigned from the scoring table to each of the patient indicators from each of the plurality of patients. The assigned scores can be summed to provide a summed population score for the patient population. The summed population scores and a plurality of mortality indicators can be used to provide a mortality risk for the patient population. Similar analyses may be performed, for example, for residents of a nursing home, soldiers in a military field hospital or people in an ambulatory care setting.

In some instances, the various indicators may be correlated to each other to provide the interrelationship between the indicators and/or select suitable indicators for use in assessing mortality risk. For example, linear or non-linear models can be implemented with the scores and/or indicators to provide a threshold value or output that may be used in assessing mortality risk. In some instances, non-linear models or neural models may be more desirable to implement to assess the mortality risk of a particular patient or patient population. In some embodiments, a non-linear regression analysis, e.g., successive approximations, ordinary least squares, weighted least squares, etc. can be implemented to assess mortality risk. In other configurations, a partitioning model may be implemented to use the scores and/or indicators and assess mortality of a patient or patient population. For example, a partitioning model, e.g., a classification tree, can be used to capture complicated interactions between the variables, e.g., scores or indicators. This method permits, for example, individual indicators that impact morality to be easily identified.

In other instances, a neural network model, e.g., an artificial neural network, can be implemented to assess mortality risks. In a typical neural network, a plurality of interconnected nodes or neurons can be used. In some instances, one, two or three layers (or more) may be present in the network with a first layer configured to output data to a second layer, which can output to a third layer. The interconnected nature of the nodes permits extraction of patterns to detect complicated trends that are too complex to be apparent or realized in simple linear or non-linear models. In some instances, the node(s) can be used to calculate a weighted sum of the inputs and compare it to a threshold value.

In some embodiments, a mortality risk score or threshold value may be assigned to various ambulatory care units, e.g., by nursing staff or other staff. The threshold value can be set and may vary from unit to unit. For example, a threshold value of above 1 may signify substantial mortality risk, whereas a threshold value below 1 may signify less mortality risk. The particular threshold values provided may be color-coded, as noted herein for other scores, to permit rapid visual feedback to staff. In some instances, patients with a threshold value above a selected value may be color-coded red, those with a threshold value within an interval below the threshold value may be color-coded yellow and those with a threshold value below the interval may be color-coded green.

In certain configurations, indicators that may be particularly suited for use in assessing mortality risk (referred to herein as mortality indicators) include one, two, three, four, five, six, seven, eight or more of the following indicators or values: maximum time of stay, age of patient, mean acuity total score, mean systolic blood pressure, mean Glasgow coma score or Neurological Status, mean urine output, median acuity total score, median systolic blood pressure, median Glasgow coma score or neurological status, median urine output, minimum acuity total score, minimum systolic blood pressure, minimum Glasgow coma score or Neurological Status, minimum urine output, maximum acuity total score, maximum systolic blood pressure, maximum Glascow coma score or Neurological Status, maximum urine output, range acuity total score, range systolic blood pressure, range Glasgow coma score or Neurological Status, range urine output, gender or other indicators described herein depending on a particular patient's health status and/or condition.

It will be recognized by the person of ordinary skill in the art, given the benefit of this disclosure, that the systems described herein may include additional components, may be coupled to additional systems and may otherwise be altered in other manners to permit scoring of indicators using empirical information. In some embodiments, the scoring systems and methods described herein may be packaged with or integrated into an electronic medical record system. For example, an electronic medical record system may include a module or menu selection that can permit implementation of the systems and methods described herein.

Certain specific examples are provided below to illustrate further some of the novel aspects and features of the technology described herein.

EXAMPLE 1

Figure 26:
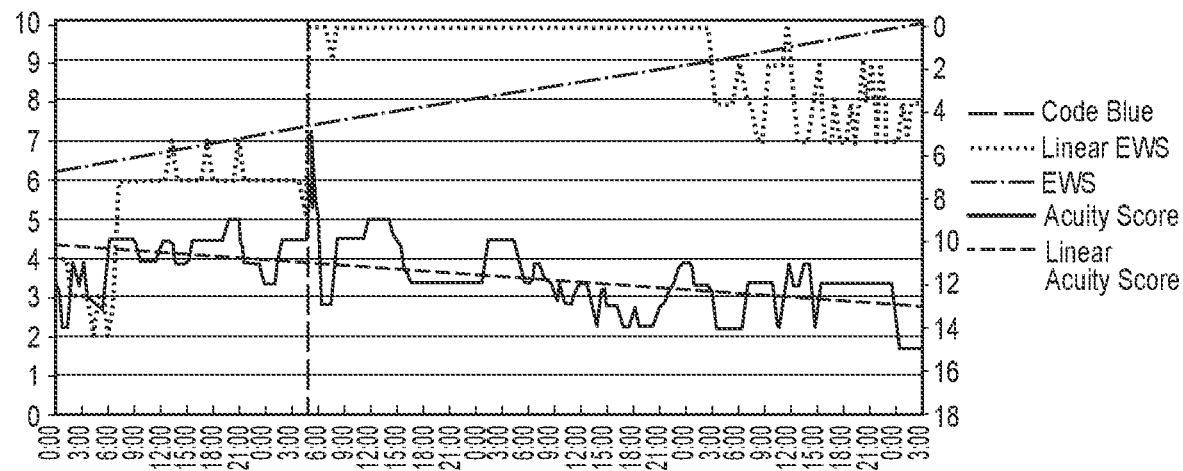
FIG. 26 is a graph showing the compressed patient indicator score (labeled as acuity score) as a function of time and an early warning score (EWS) for the same patient, in accordance with certain examples.

The following example used actual patient indicators. A patient was admitted on a step-down/progressive care unit with primary problem of hypoxia. Over the next 48 hours the patient's compressed, composite patient indicator score was calculated from patient indicators. The compressed, composite patient indicator score almost doubled from a score of 4 to approximately 7 over the course of the next 30 hours prior to the patient arresting (see FIG. 26). The increase in the compressed score also corresponded to an early warning score derived at the same time frame. During the same time period, there were no key indicators necessitating that the patient received additional interventions due to the subtle signs of change across multiple shifts and care providers. If the scoring system described herein would have been available for the care team, there potentially could have been additional resources applied to the patient for earlier intervention or rapid response prior to an arrest and subsequent move to the intensive care unit. Upon continued evaluation the early warning score reflected a false positive of improvement following the patient for the next 4 days while the compressed patient indicator score continued to more clearly reflect the patient's status and care requirements. The early warning score appears to be unable to detect changes from electronic documentation and intervention to sustain the patient's scores, e.g., intubation creates a false positive score for the early warning score tool.

EXAMPLE 2

Figure 27:
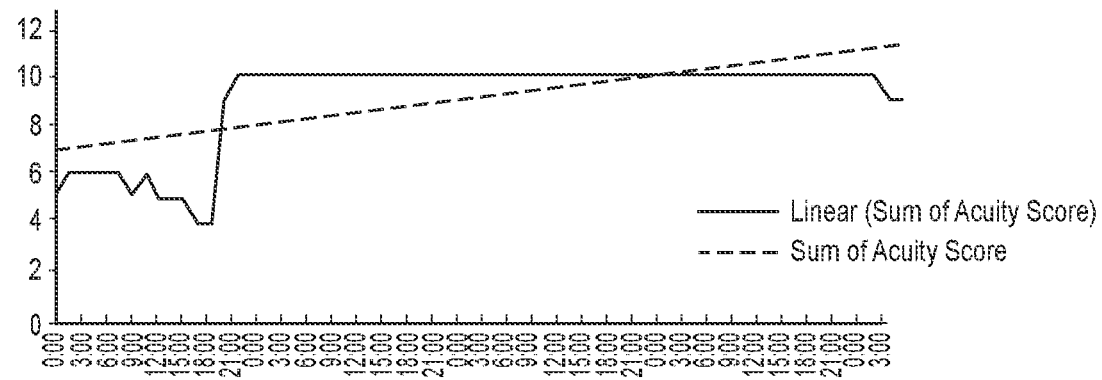
FIG. 27 is a graph showing the compressed patient indicator score (labeled as acuity score) as a function of time, in accordance with certain examples.

The following example used actual patient indicators. A patient arrived at the hospital with a compressed, composite patient indicator score in the caution range, e.g., above 5 (see FIG. 27). Over the next 12-13 hours the patient experienced an approximate 50% increase in their compressed, composite patient indicator score. The patient arrested at approximately 0230 the following day. The care team documentation crossing multiple shifts does not indicate the team had sufficient information to identify potential changes in the patient condition. If the score would have been available to care team, there may have been an opportunity to intervene with additional resources and intervention on the patient's behalf at least 6 hours prior to the arresting event. These interventions may have been able to prevent a longer length of stay and better overall outcome for the patient.

EXAMPLE 3

Patients' acuity and workload indicator scores are trended over time with composite patient indicator scores monitored prior to discharge. If a composite score for patients prior to discharge and throughout the patient's care team the possibility exists that readmission rates for hospitalization could be reduced significantly by additional resources applied during the hospitalization or closer monitoring in a home or ambulatory setting. FIG. 28 shows a graph comparing the composite scores of patients (4 hours prior to discharge or death) that died, patients that were discharged (DC) and patients with a 30-day readmission. The percentage of patients with a particular score range is shown on the y-axis. The scores prior to discharge may be reviewed to assess whether the patient is more likely to need readmission and follow up treatment and/or monitoring may be scheduled to reduce the likelihood of discharge.

EXAMPLE 4

Composite patient indicator scores can be updated real-time based on documentation and captured hourly to determine population scores. These population scores are then translated into clinical resource skill mix, e.g., RN, LPN, nursing assistant, etc., needed to care for a group of cohorted patients with varying scores. Four hour score totals are update hourly and projected out the next 24 hours of resources necessary to care for the group of cohorted patients. Traditional resource models are based in subjective or purely census calculations. Although the census in two intensive care units may be 12, the population score may be doubled in unit one compared to unit two. A color coded output and various alert signals can be sent to administrative resources when resources vary from a projected level by a standard deviation. Table 10 in FIG. 28 shows an example of suggested staffing levels for a particular unit.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

EXAMPLE 5

A representative listing of scores for various assessments is shown in the tables of FIGS. 29A-29F. For example, neurological, cardiovascular, peripheral vascular, skin, gastrointestinal, genitourinary, psychosocial, head and neck, musculoskeletal or other system based assessments may be performed and used in the various scoring and subscoring methods and systems described herein. While many different assessments are shown, not necessarily all of the scores from the assessment will be used for a particular patient. Depending on patient population, patient age, weight, gender or other factors, it may be desirable to only use 1, 2, 3, 4, or 5 of the categories shown in FIGS. 29A-29F.

EXAMPLE 6

Referring to FIG. 30, a table is shown of compresses scores and intervention/resource coding. As can be seen, the compressed score for patient C is 10 and color-coded red, but the intervention needed, which may be determined in many different manners including the use of a subscore, is low. Similarly, the compressed score for patient A is in the mid-level range, but the intervention/resource level is high. It may be that one or more subscores indicate that patient A is in need of additional staff resources even though the overall compressed score would not provide the same result.

EXAMPLE 7

To assess the ability to predict mortality using the indicators and scores described herein, a neural network model was implemented. Patients 18 and older seen at one of 8 acute care facilities ranging from a large academic medical center to critical access facilities were included in initial validation of the mortality prediction tool. Phase one analysis included all patients 18 years and older seen at an acute Care facility across a 12 month time frame (approximately 30,000 patients total). Seventy-seven clinical indicators were captured hourly from 154,452 care episodes. Indicators were derived from existing objective nursing and clinical documentation.

A neural network model was implemented to determine a threshold value for mortality. The model developed consisted of interconnected groups of artificial neurons that process information, adapt and learn. This allowed for modeling of complex relationships between inputs and output in the data. Utilizing this method, the model was determined to be an identical match. The model received multiple inputs, identified hidden neurons and produced an output. The model was predictive of mortality upon discharge to 7/10 of 1 percent or 0.007 or 99.3% accuracy. The model allows the care setting to set the threshold of tolerance for false positive and negatives associated with mortality predictability (see FIG. 31). For example, the model will produce a value for a patient, which may be calculated on a desired basis such as, for example, hourly, each half-hour, every two hours, every four hours, etc. If the patient value is bigger than the defined threshold, an alarm can trigger.

In testing the model, the following indicators were used to determine a threshold value for mortality.

Input nodes H1 each have an output:
Maximum Hour of Stay
Age of patient
Mean Acuity total score
Mean Systolic Blood Pressure
Mean Glascow coma score or Neurological Status
Mean Urine Output Median
Acuity total score Median
Systolic Blood Pressure
Median Glascow coma score or Neurological Status
Median Urine Output
Min Acuity total score
Min Systolic Blood Pressure
Min Glascow coma score or Neurological Status
Min Urine Output
Max Acuity total score
MaxSystolic Blood Pressure
Max Glascow coma score or Neurological Status
Max Urine Output
Range Acuity total score
Range Systolic Blood Pressure
Range Glascow coma score or Neurological Status
Range Urine Output
Gender Female
Gender Male
Input nodes H2 each have an output:
Maximum Hour of Stay
Age of patient
Mean Acuity total score
Mean Systolic Blood Pressure
Mean Glascow coma score or Neurological Status
Mean Urine Output Median
Acuity total score Median
Systolic Blood Pressure
Median Glascow coma score or Neurological Status
Median Urine Output
Min Acuity total score
Min Systolic Blood Pressure
Min Glascow coma score or Neurological Status
Min Urine Output
Max Acuity total score
MaxSystolic Blood Pressure
Max Glascow coma score or Neurological Status
Max Urine Output
Range Acuity total score
Range Systolic Blood Pressure
Range Glascow coma score or Neurological Status
Range Urine Output Gender Female
Gender Male
Intercept In the neural network, 24 H2_XX nodes were implemented with inputs are as indicated above. Max(HS)=length of stay, others are gender, age and indices, plus an intercept. Each input is a linear combination, with the coefficient. The output of a node is Tan $H(x)=[\exp(2x)-1]/[\exp(2x)+1]$ where x is the input. There may be 12 H1_XX nodes, each of whose inputs is a linear combination of the outputs of the H2 XX nodes, with various coefficients. The final prediction is a linear combination of the outputs of the 12 H1_xx nodes. The range of the output prediction produces a series of thresholds that can be adjusted as desired.

Figure 32:
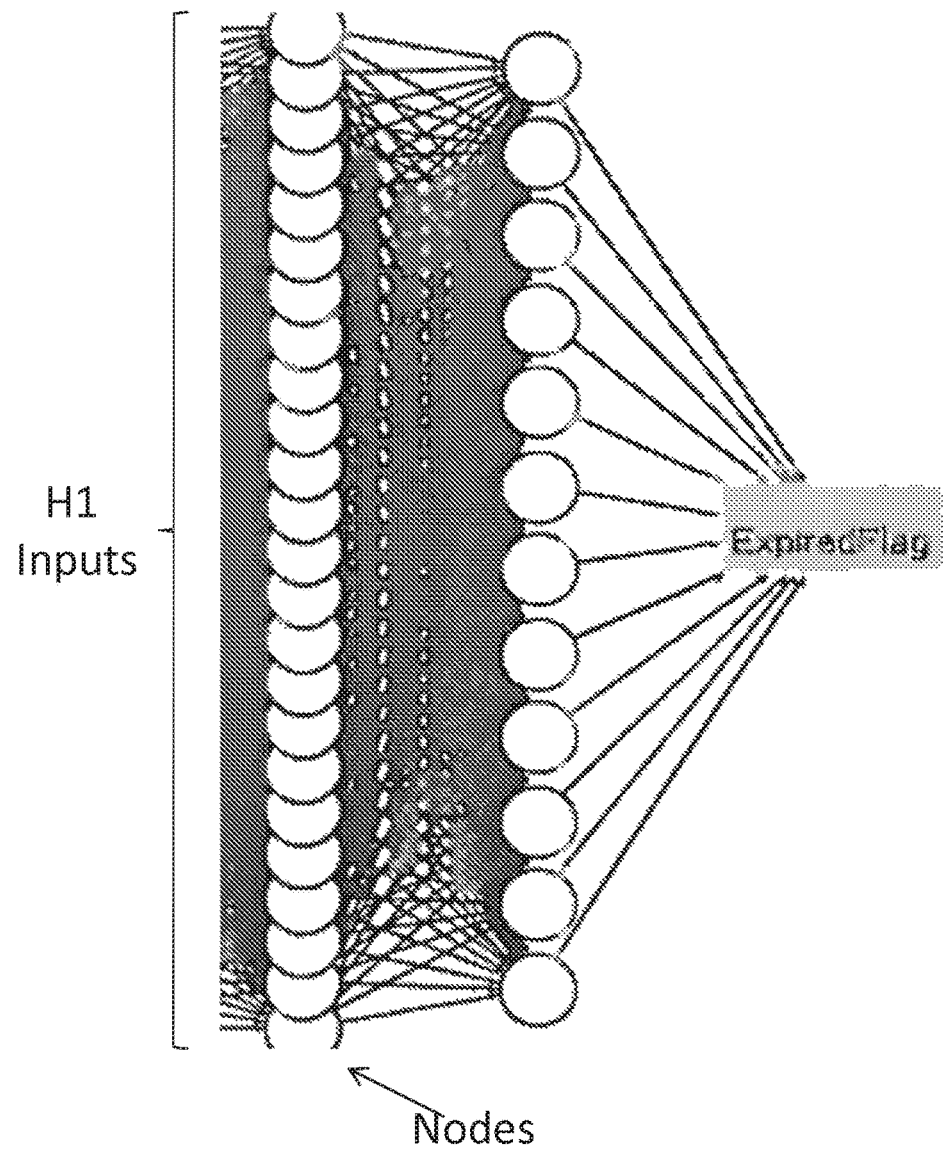
FIG. 32 is a schematic showing the nodes of the neural network.
Figure 33:
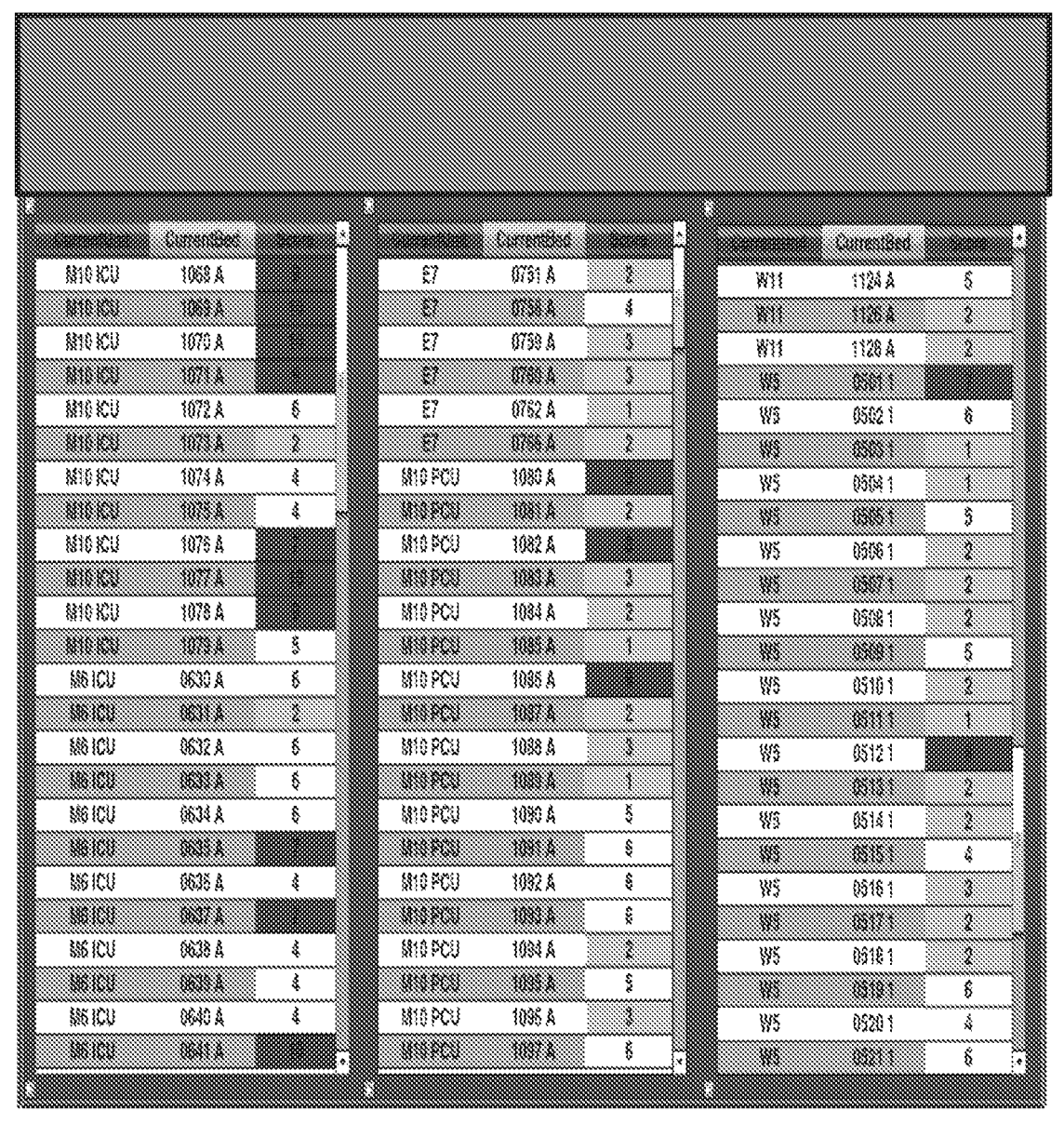
Figure 34:
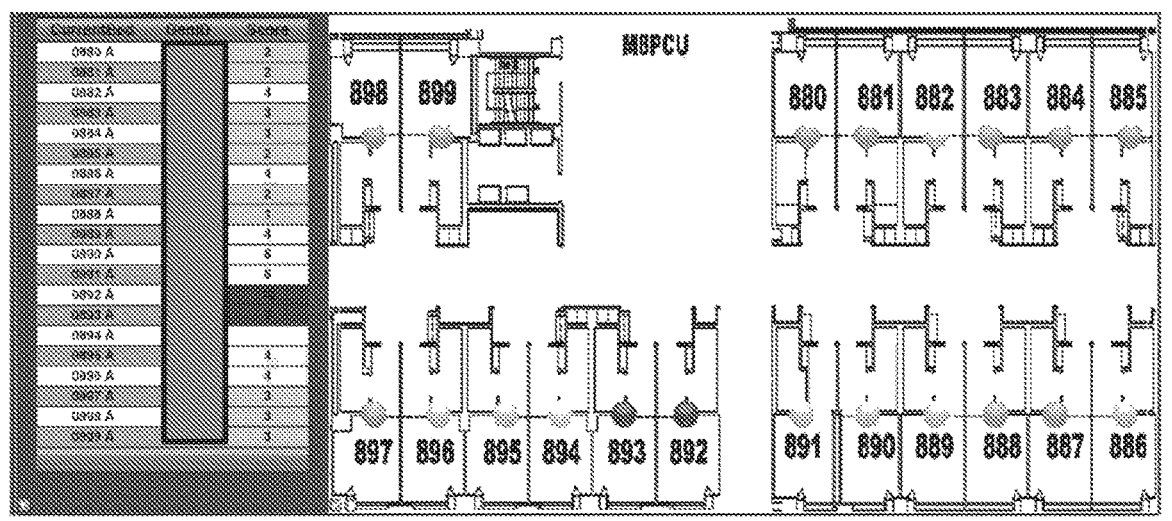
FIG. 34 shows the bed and score along with a room layout with overlayed score.

A general schematic of the nodes of the model is shown in FIG. 32. Each of the 24 nodes has an input (data flow left to right). Each of 24 nodes has inputs that are the linear combinations of the values of the input variables. The coefficients are estimated by the model. For the H2_1 to 24 inputs, the output is a hyperbolic tangent function of the input. The first group to an intercept are how input variables are combined to get the input to H2_1. All input variables including intercept are the hyperbolic tangents of the input. This process gets repeated 24 times due to the presence of 24 nodes. Each node regardless of its position in the first layer it is in gets an input that is a linear combination of the coefficients and computes hyperbolic tangent. The hyperbolic tangent is provided from the 24 nodes to the 12 nodes of the second layer of the model. A third and final layer computes the predicted value of the expired flag. This last node is a linear combination of inputs which are the outputs of the second layer, and outputs of the second layer are hyperbolic tangents. The combination of the hyperbolic tangent output creates a predicted output of the expired flag, which is referred to herein as a mortality risk value. In certain embodiments, the output from the neural network model may be scaled on a scale of 1 to 3 and color coded, if desired, e.g., 1 being low risk, 2 being medium risk and 3 being high risk. The mortality risk may be displayed along with the scaled scores (see FIG. 33), which may also be color-coded. If desired the scaled scores and/or mortality risk values can be placed on a dashboard or floor level room representation (see FIG. 34) to provide for rapid visual feedback to staff of those patients who may have a higher mortality risk.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A method, implemented in a computing device, the method comprising:
   retrieving patient data for a plurality of patients assigned to a healthcare unit of a medical facility;
   scoring a mortality risk of the patients from the patient data, comprising:
      applying respective weights to each of a plurality of health indicators for each of the patients, the respective weights controlling a respective contribution of each of the health indicators to a composite patient indicator representing the patient's mortality risk;
      periodically determining, for each of the patients, the composite patient indicator representing the patient's mortality risk and responsive to the composite patient indicator of a patient exceeding a threshold, triggering an alert to indicate a mortality prediction for the patient;
      periodically scoring the mortality risk based on the periodic determination of the composite patient indicators;
      extrapolating a trend from the periodic scoring of the mortality risk; and
      based on the trend, determining a future time in which to propose that a staffing level of the healthcare unit be changed;
   generating a map of the medical facility comprising:
      an illustration of a layout of the medical facility;
      a visual representation of an area within the illustration of the layout that indicates where the healthcare unit is located within the medical facility; and
      a labeling of the healthcare unit with a visual indication of the mortality risk of the patients in the healthcare unit; and
   sending the map to a display device.

2. The method of claim 1, further comprising determining a staffing level of the healthcare unit based on the mortality risk, and sending an indication of the staffing level of the healthcare unit to the display device.

3. The method of claim 2, wherein determining the staffing level of the healthcare unit based on the mortality risk comprises determining a numbers of licensed and unlicensed staff for the healthcare unit.

4. The method of claim 1, wherein generating the map of the medical facility comprises generating an overhead map of the medical facility, such that the illustration of the layout of the medical facility depicts a floorplan on a floor of the medical facility.

5. The method of claim 1, wherein generating the map of the medical facility comprises generating a side-view map of the medical facility, such that the illustration of the layout of the medical facility depicts a schematic of different floors of the medical facility.

6. The method of claim 1, wherein the visual indication of the mortality risk comprises one of a plurality of differently colored icons, each of the differently colored icons representing a respective risk severity.

7. A computing device comprising:
   interface circuitry configured to interface with a database comprising patient data for a plurality of patients assigned to a healthcare unit of a medical facility;
   processing circuitry communicatively coupled to the interface circuitry and configured to:
      retrieve patient data for a plurality of patients assigned to the healthcare unit of the medical facility;
      score a mortality risk of the patients from the patient data, comprising:
         applying respective weights to each of a plurality of health indicators for each of the patients, the respective weights controlling a respective contribution of each of the health indicators to a composite patient indicator representing the patient's mortality risk;
         periodically determining, for each of the patients, the composite patient indicator representing the patient's mortality risk and responsive to the composite patient indicator of a patient exceeding a threshold, triggering an alert to indicate a mortality prediction for the patient;
         periodically scoring the mortality risk based on the periodic determination of the composite patient indicators;

extrapolating a trend from the periodic scoring of the mortality risk; and based on the trend, determining a future time in which to propose that a staffing level of the healthcare unit be changed;

generate a map of the medical facility comprising:
an illustration of a layout of the medical facility;
a visual representation of an area within the illustration of the layout that indicates where the healthcare unit is located within the medical facility; and
a labeling of the healthcare unit with a visual indication of the mortality risk of the patients in the healthcare unit; and send the map to a display device.

8. The computing device of claim 7, wherein the processing circuitry is further configured to determine a staffing level of the healthcare unit based on the mortality risk, and send an indication of the staffing level of the healthcare unit to the display device.

9. The computing device of claim 8, wherein to determine the staffing level of the healthcare unit based on the mortality risk, the processing circuitry is configured to determine a numbers of licensed and unlicensed staff for the healthcare unit.

10. The computing device of claim 7, wherein to generate the map of the medical facility, the processing circuitry is configured to generate an overhead map of the medical facility, such that the illustration of the layout of the medical facility depicts a floorplan on a floor of the medical facility.

11. The computing device of claim 7, wherein to generate the map of the medical facility, the processing circuitry is configured to generate a side-view map of the medical facility, such that the illustration of the layout of the medical facility depicts a schematic of different floors of the medical facility.

12. The computing device of claim 7, wherein the visual indication of the mortality risk comprises one of a plurality of differently colored icons, each of the differently colored icons representing a respective risk severity.

13. A non-transitory computer readable medium storing a computer program product for controlling a programmable computing device, the computer program product comprising software instructions that, when run on the programmable computing device, cause the programmable computing device to:

retrieve patient data for a plurality of patients assigned to a healthcare unit of a medical facility;

score a mortality risk of the patients from the patient data, comprising:
applying respective weights to each of a plurality of health indicators for each of the patients, the respective weights controlling a respective contribution of each of the health indicators to a composite patient indicator representing the patient's mortality risk;
periodically determining, for each of the patients, the composite patient indicator representing the patient's mortality risk and responsive to the composite patient indicator of a patient exceeding a threshold, triggering an alert to indicate a mortality prediction for the patient;
periodically scoring the mortality risk based on the periodic determination of the composite patient indicators;
extrapolating a trend from the periodic scoring of the mortality risk; and based on the trend, determining a future time in which to propose that a staffing level of the healthcare unit be changed;

generate a map of the medical facility comprising:
an illustration of a layout of the medical facility;
a visual representation of an area within the illustration of the layout that indicates where the healthcare unit is located within the medical facility; and
a labeling of the healthcare unit with a visual indication of the mortality risk of the patients in the healthcare unit; and send the map to a display device.

* * * * *